United States Patent
Majdoul et al.

(10) Patent No.: US 11,371,061 B2
(45) Date of Patent: Jun. 28, 2022

(54) COMPOSITIONS AND METHODS FOR IMPROVING VIRAL VECTOR EFFICIENCY

(71) Applicants: GENETHON, Evry (FR); INSERM (INSTITUT NATIONAL DE LA SANTÉ ET DE LA RECHERCHE MÉDICALE), Paris (FR); UNIVERSITE D'EVRY VAL D'ESSONNE, Evry (FR)

(72) Inventors: Saliha Majdoul, Massy (FR); David Fenard, Antibes (FR)

(73) Assignees: GENETHON, Evry (FR); INSERM (INSTITUT NATIONAL DE LA SANTE ET DE LA RECHERCHE MEDICALE), Paris (FR); UNIVERSITE D'EVRY VAL D'ESSONNE, Evry (FR)

( * ) Notice: Subject to any disclaimer, the term of this patent is extended or adjusted under 35 U.S.C. 154(b) by 430 days.

(21) Appl. No.: 15/772,902

(22) PCT Filed: Nov. 30, 2016

(86) PCT No.: PCT/EP2016/079304
§ 371 (c)(1),
(2) Date: May 2, 2018

(87) PCT Pub. No.: WO2017/093330
PCT Pub. Date: Jun. 8, 2017

(65) Prior Publication Data
US 2018/0318447 A1 Nov. 8, 2018

(30) Foreign Application Priority Data
Dec. 3, 2015 (EP) .................................. 15306924
Oct. 17, 2016 (EP) .................................. 16194180

(51) Int. Cl.
| C12N 15/87 | (2006.01) |
| C12N 15/86 | (2006.01) |
| C07K 14/82 | (2006.01) |
| A61K 48/00 | (2006.01) |
| C07K 14/47 | (2006.01) |

(52) U.S. Cl.
CPC .......... *C12N 15/87* (2013.01); *A61K 48/0016* (2013.01); *C07K 14/47* (2013.01); *C07K 14/82* (2013.01); *C12N 15/86* (2013.01); *C07K 2319/033* (2013.01); *C07K 2319/10* (2013.01); *C12N 2740/15011* (2013.01); *C12N 2740/15041* (2013.01); *C12N 2740/15043* (2013.01); *C12N 2750/14141* (2013.01); *C12N 2750/14143* (2013.01); *C12N 2750/14311* (2013.01)

(58) Field of Classification Search
CPC .......... C07K 2319/10; C07K 2319/033; C12N 15/87
See application file for complete search history.

(56) References Cited

U.S. PATENT DOCUMENTS

| 2014/0066382 A1* | 3/2014 | Levine ..................... A61P 31/00 514/18.9 |
| 2019/0225966 A1* | 7/2019 | Zode ..................... A61K 31/436 |
| 2019/0382443 A1* | 12/2019 | Kritzer ............... C07K 14/4747 |
| 2020/0230207 A1* | 7/2020 | Settembre ............ A61K 31/436 |
| 2021/0138035 A1* | 5/2021 | Borjas ................. C12N 9/1077 |

FOREIGN PATENT DOCUMENTS

| WO | 2011/106684 A2 | 9/2011 |
| WO | 2013/119377 A1 | 8/2013 |
| WO | 2014/109728 A1 | 7/2014 |
| WO | 2015/042272 A1 | 3/2015 |
| WO | 2016/119856 A1 | 8/2016 |

OTHER PUBLICATIONS

Of Zhang et al. Cell Death and Disease 10;419, 2019.pp. 1-14 (Year: 2019).*
Majdoul et al. JBC 282(45):18672-18681, 2017 (Year: 2017).*
Sanae Shoji-Kawata et al: "Identification of a candidate therapeutic autophagy-inducing peptide", Nature, vol. 494, No. 7436, Jan. 30, 2013 (Jan. 30, 2013), pp. 201-206, XP055225704,United Kingdom ISSN: 0028-0836, DOI: 10.1038/nature11866.
Wang Yang et al: "A novel antitumour strategy using bidirectional autophagic vesicles accumulation via initiative induction and the terminal restraint of autophagic flux", Journal of Controlled Release, vol. 199, Dec. 10, 2014 (Dec. 10, 2014), pp. 17-28, XP029190821, ISSN: 0168-3659, DOI: 10.1016/J.JCONREL.2014.12.005.
International Search Report for PCT/EP2016/079304 and Written Opinion, dated Mar. 6, 2017.

* cited by examiner

*Primary Examiner* — Marcia S Noble
(74) *Attorney, Agent, or Firm* — W&C IP

(57) ABSTRACT

The present invention relates to peptides and compositions for use in improving transduction efficiency of viruses into target cells.

11 Claims, 8 Drawing Sheets

Figure 1:
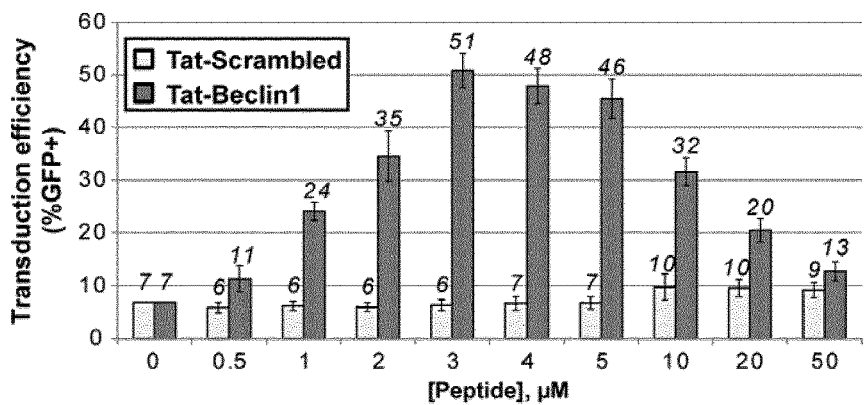
Figure 1:
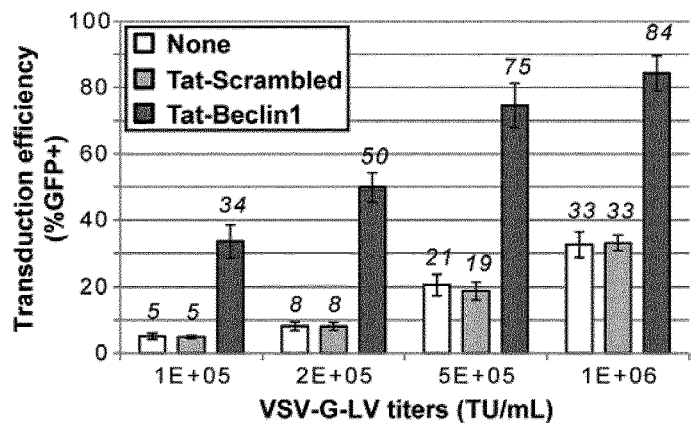
Figure 1:
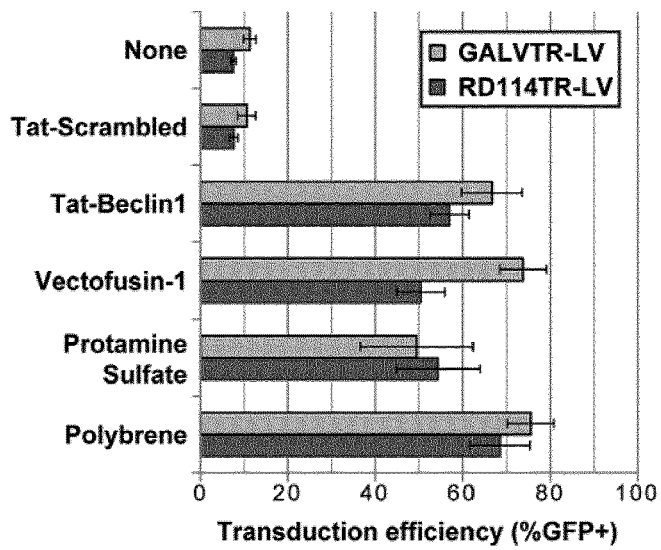

Specification includes a Sequence Listing.

A

B

C

SEQUENCE LISTING

<160> NUMBER OF SEQ ID NOS: 102

<210> SEQ ID NO 1
<211> LENGTH: 11
<212> TYPE: PRT

```
<213> ORGANISM: artificial
<220> FEATURE:
<223> OTHER INFORMATION: Synthetic Tat (47-57)

<400> SEQUENCE: 1

Tyr Gly Arg Lys Lys Arg Arg Gln Arg Arg
1               5                   10

<210> SEQ ID NO 2
<211> LENGTH: 13
<212> TYPE: PRT
<213> ORGANISM: artificial
<220> FEATURE:
<223> OTHER INFORMATION: Synthetic Tat (48-60)

<400> SEQUENCE: 2

Gly Arg Lys Lys Arg Arg Gln Arg Arg Arg Pro Pro Gln
1               5                   10

<210> SEQ ID NO 3
<211> LENGTH: 9
<212> TYPE: PRT
<213> ORGANISM: artificial
<220> FEATURE:
<223> OTHER INFORMATION: Synthetic Tat (49-57)

<400> SEQUENCE: 3

Arg Lys Lys Arg Arg Gln Arg Arg Arg
1               5

<210> SEQ ID NO 4
<211> LENGTH: 17
<212> TYPE: PRT
<213> ORGANISM: artificial
<220> FEATURE:
<223> OTHER INFORMATION: Synthetic MAP peptide

<400> SEQUENCE: 4

Lys Leu Ala Leu Lys Leu Ala Leu Lys Ala Leu Lys Ala Ala Leu Lys
1               5                   10                  15

Ala

<210> SEQ ID NO 5
<211> LENGTH: 18
<212> TYPE: PRT
<213> ORGANISM: artificial
<220> FEATURE:
<223> OTHER INFORMATION: Synthetic MAP peptide

<400> SEQUENCE: 5

Lys Leu Ala Leu Lys Leu Ala Leu Lys Ala Leu Lys Ala Ala Leu Lys
1               5                   10                  15

Leu Ala

<210> SEQ ID NO 6
<211> LENGTH: 16
<212> TYPE: PRT
<213> ORGANISM: artificial
<220> FEATURE:
<223> OTHER INFORMATION: Synthetic Antennapedia (or penetratin)

<400> SEQUENCE: 6

Arg Gln Ile Lys Ile Trp Phe Gln Asn Arg Arg Met Lys Trp Lys Lys
1               5                   10                  15
```

```
<210> SEQ ID NO 7
<211> LENGTH: 7
<212> TYPE: PRT
<213> ORGANISM: artificial
<220> FEATURE:
<223> OTHER INFORMATION: Synthetic Penetratin derivative

<400> SEQUENCE: 7

Arg Arg Met Lys Trp Lys Lys
1               5

<210> SEQ ID NO 8
<211> LENGTH: 8
<212> TYPE: PRT
<213> ORGANISM: artificial
<220> FEATURE:
<223> OTHER INFORMATION: Synthetic Penetratin derivative

<400> SEQUENCE: 8

Asn Arg Arg Met Lys Trp Lys Lys
1               5

<210> SEQ ID NO 9
<211> LENGTH: 9
<212> TYPE: PRT
<213> ORGANISM: artificial
<220> FEATURE:
<223> OTHER INFORMATION: Synthetic Penetratin derivative

<400> SEQUENCE: 9

Gln Asn Arg Arg Met Lys Trp Lys Lys
1               5

<210> SEQ ID NO 10
<211> LENGTH: 10
<212> TYPE: PRT
<213> ORGANISM: artificial
<220> FEATURE:
<223> OTHER INFORMATION: Synthetic Penetratin derivative

<400> SEQUENCE: 10

Phe Gln Asn Arg Arg Met Lys Trp Lys Lys
1               5                   10

<210> SEQ ID NO 11
<211> LENGTH: 7
<212> TYPE: PRT
<213> ORGANISM: artificial
<220> FEATURE:
<223> OTHER INFORMATION: Synthetic Penetratin derivative

<400> SEQUENCE: 11

Arg Arg Glu Lys Trp Lys Lys
1               5

<210> SEQ ID NO 12
<211> LENGTH: 7
<212> TYPE: PRT
<213> ORGANISM: artificial
<220> FEATURE:
<223> OTHER INFORMATION: Synthetic Penetratin derivative

<400> SEQUENCE: 12

Arg Arg Gln Lys Trp Lys Lys
1               5

<210> SEQ ID NO 13
```

```
<211> LENGTH: 7
<212> TYPE: PRT
<213> ORGANISM: artificial
<220> FEATURE:
<223> OTHER INFORMATION: Synthetic Penetratin derivative

<400> SEQUENCE: 13

Lys Arg Met Lys Trp Lys Lys
1               5

<210> SEQ ID NO 14
<211> LENGTH: 7
<212> TYPE: PRT
<213> ORGANISM: artificial
<220> FEATURE:
<223> OTHER INFORMATION: Synthetic Penetratin derivative

<400> SEQUENCE: 14

Arg Lys Met Lys Trp Lys Lys
1               5

<210> SEQ ID NO 15
<211> LENGTH: 7
<212> TYPE: PRT
<213> ORGANISM: artificial
<220> FEATURE:
<223> OTHER INFORMATION: Synthetic Penetratin derivative
<220> FEATURE:
<221> NAME/KEY: MISC_FEATURE
<222> LOCATION: (3)..(3)
<223> OTHER INFORMATION: X = ornithine

<400> SEQUENCE: 15

Arg Arg Xaa Lys Trp Lys Lys
1               5

<210> SEQ ID NO 16
<211> LENGTH: 7
<212> TYPE: PRT
<213> ORGANISM: artificial
<220> FEATURE:
<223> OTHER INFORMATION: Synthetic Penetratin derivative

<400> SEQUENCE: 16

Arg Arg Met Lys Gln Lys Lys
1               5

<210> SEQ ID NO 17
<211> LENGTH: 7
<212> TYPE: PRT
<213> ORGANISM: artificial
<220> FEATURE:
<223> OTHER INFORMATION: Synthetic Penetratin derivative

<400> SEQUENCE: 17

Arg Arg Met Lys Trp Phe Lys
1               5

<210> SEQ ID NO 18
<211> LENGTH: 7
<212> TYPE: PRT
<213> ORGANISM: artificial
<220> FEATURE:
<223> OTHER INFORMATION: Synthetic Penetratin derivative
<220> FEATURE:
<221> NAME/KEY: MISC_FEATURE
<222> LOCATION: (2)..(2)
<223> OTHER INFORMATION: Xaa=Orn
```

```
<400> SEQUENCE: 18

Arg Xaa Arg Lys Trp Lys Lys
1               5

<210> SEQ ID NO 19
<211> LENGTH: 7
<212> TYPE: PRT
<213> ORGANISM: artificial
<220> FEATURE:
<223> OTHER INFORMATION: Synthetic Penetratin derivative

<400> SEQUENCE: 19

Arg Arg Met Trp Lys Lys Lys
1               5

<210> SEQ ID NO 20
<211> LENGTH: 7
<212> TYPE: PRT
<213> ORGANISM: artificial
<220> FEATURE:
<223> OTHER INFORMATION: Synthetic Penetratin derivative

<400> SEQUENCE: 20

Arg Arg Met Lys Lys Trp Lys
1               5

<210> SEQ ID NO 21
<211> LENGTH: 16
<212> TYPE: PRT
<213> ORGANISM: artificial
<220> FEATURE:
<223> OTHER INFORMATION: Synthetic D-penetratin
<220> FEATURE:
<221> NAME/KEY: MISC_FEATURE
<222> LOCATION: (1)..(16)
<223> OTHER INFORMATION: D-amino acid

<400> SEQUENCE: 21

Arg Gln Ile Lys Ile Trp Phe Gln Asn Arg Arg Met Lys Trp Lys Lys
1               5                   10                  15

<210> SEQ ID NO 22
<211> LENGTH: 18
<212> TYPE: PRT
<213> ORGANISM: artificial
<220> FEATURE:
<223> OTHER INFORMATION: Synthetic Pegelin (SynB)

<400> SEQUENCE: 22

Arg Gly Gly Arg Leu Ser Tyr Ser Arg Arg Arg Phe Ser Thr Ser Thr
1               5                   10                  15

Gly Arg

<210> SEQ ID NO 23
<211> LENGTH: 33
<212> TYPE: PRT
<213> ORGANISM: artificial
<220> FEATURE:
<223> OTHER INFORMATION: Synthetic VP22

<400> SEQUENCE: 23

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Val
                20                  25                  30
```

Asp

<210> SEQ ID NO 24
<211> LENGTH: 27
<212> TYPE: PRT
<213> ORGANISM: artificial
<220> FEATURE:
<223> OTHER INFORMATION: Synthetic Transportan

<400> SEQUENCE: 24

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 25
<211> LENGTH: 21
<212> TYPE: PRT
<213> ORGANISM: artificial
<220> FEATURE:
<223> OTHER INFORMATION: Synthetic Transportan-10

<400> SEQUENCE: 25

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 26
<211> LENGTH: 30
<212> TYPE: PRT
<213> ORGANISM: artificial
<220> FEATURE:
<223> OTHER INFORMATION: Synthetic KALA

<400> SEQUENCE: 26

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 27
<211> LENGTH: 21
<212> TYPE: PRT
<213> ORGANISM: artificial
<220> FEATURE:
<223> OTHER INFORMATION: Synthetic Pep-1

<400> SEQUENCE: 27

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 28
<211> LENGTH: 21
<212> TYPE: PRT
<213> ORGANISM: artificial
<220> FEATURE:
<223> OTHER INFORMATION: Synthetic Pep-2

<400> SEQUENCE: 28

Lys Glu Thr Trp Phe Glu Thr Trp Phe Thr Glu Trp Ser Gln Pro Lys
1               5                   10                  15

```
Lys Lys Arg Lys Val
            20

<210> SEQ ID NO 29
<211> LENGTH: 27
<212> TYPE: PRT
<213> ORGANISM: artificial
<220> FEATURE:
<223> OTHER INFORMATION: Synthetic MPG

<400> SEQUENCE: 29

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 30
<211> LENGTH: 19
<212> TYPE: PRT
<213> ORGANISM: artificial
<220> FEATURE:
<223> OTHER INFORMATION: Synthetic Vectocell peptide

<400> SEQUENCE: 30

Val Lys Arg Gly Leu Lys Leu Arg His Val Arg Pro Arg Val Thr Arg
1               5                   10                  15

Met Asp Val

<210> SEQ ID NO 31
<211> LENGTH: 14
<212> TYPE: PRT
<213> ORGANISM: artificial
<220> FEATURE:
<223> OTHER INFORMATION: Synthetic Vectocell peptide

<400> SEQUENCE: 31

Ser Arg Arg Ala Arg Arg Ser Pro Arg His Leu Gly Ser Gly
1               5                   10

<210> SEQ ID NO 32
<211> LENGTH: 16
<212> TYPE: PRT
<213> ORGANISM: artificial
<220> FEATURE:
<223> OTHER INFORMATION: Synthetic Vectocell peptide

<400> SEQUENCE: 32

Leu Arg Arg Glu Arg Gln Ser Arg Leu Arg Arg Glu Arg Gln Ser Arg
1               5                   10                  15

<210> SEQ ID NO 33
<211> LENGTH: 22
<212> TYPE: PRT
<213> ORGANISM: artificial
<220> FEATURE:
<223> OTHER INFORMATION: Synthetic Vectocell peptide

<400> SEQUENCE: 33

Gly Ala Tyr Asp Leu Arg Arg Arg Glu Arg Gln Ser Arg Leu Arg Arg
1               5                   10                  15

Arg Glu Arg Gln Ser Arg
            20

<210> SEQ ID NO 34
<211> LENGTH: 29
```

```
<212> TYPE: PRT
<213> ORGANISM: artificial
<220> FEATURE:
<223> OTHER INFORMATION: Synthetic Wr-T transporter
<220> FEATURE:
<221> NAME/KEY: MISC_FEATURE
<222> LOCATION: (22)..(29)
<223> OTHER INFORMATION: D-amino acids

<400> SEQUENCE: 34

Lys Glu Thr Trp Trp Glu Thr Trp Trp Thr Glu Trp Trp Thr Glu Trp
1               5                   10                  15

Ser Gln Gly Pro Gly Arg Arg Arg Arg Arg Arg Arg

```
<210> SEQ ID NO 39
<211> LENGTH: 26
<212> TYPE: PRT
<213> ORGANISM: artificial
<220> FEATURE:
<223> OTHER INFORMATION: Synthetic LAH4 derivative

<400> SEQUENCE: 39

Arg Arg Ala Leu Leu Ala His Ala Leu His Leu Leu Ala Leu Leu Ala
1               5                   10                  15

Leu His Leu Ala His Ala Leu Arg Arg Ala
            20                  25

<210> SEQ ID NO 40
<211> LENGTH: 26
<212> TYPE: PRT
<213> ORGANISM: artificial
<220> FEATURE:
<223> OTHER INFORMATION: Synthetic LAH4 derivative

<400> SEQUENCE: 40

Lys Lys Ala Leu Leu Ala His Ala Leu Ala His Leu Ala Leu Leu Ala
1               5                   10                  15

Leu His Leu Ala Leu His Leu Lys Lys Ala
            20                  25

<210> SEQ ID NO 41
<211> LENGTH: 26
<212> TYPE: PRT
<213> ORGANISM: artificial
<220> FEATURE:
<223> OTHER INFORMATION: Synthetic LAH4 derivative

<400> SEQUENCE: 41

Lys Lys Ala Leu Leu Ala Leu Ala Leu His His Leu Ala Leu Leu Ala
1               5                   10                  15

Leu His Leu Ala His Ala Leu Lys Lys Ala
            20                  25

<210> SEQ ID NO 42
<211> LENGTH: 26
<212> TYPE: PRT
<213> ORGANISM: artificial
<220> FEATURE:
<223> OTHER INFORMATION: Synthetic LAH4 derivative

<400> SEQUENCE: 42

Lys Lys Ala Leu Leu Ala Leu Ala Leu His His Leu Ala Leu Leu Ala
1               5                   10                  15

His His Leu Ala Leu Ala Leu Lys Lys Ala
            20                  25

<210> SEQ ID NO 43
<211> LENGTH: 26
<212> TYPE: PRT
<213> ORGANISM: artificial
<220> FEATURE:
<223> OTHER INFORMATION: Synthetic LAH4 derivative

<400> SEQUENCE: 43

Lys Lys Ala Leu Leu His Leu Ala Leu Leu His Ala Ala Leu Leu Ala
1               5                   10                  15

His His Leu Ala Leu Ala Leu Lys Lys Ala
            20                  25
```

<210> SEQ ID NO 44
<211> LENGTH: 26
<212> TYPE: PRT
<213> ORGANISM: artificial
<220> FEATURE:
<223> OTHER INFORMATION: Synthetic LAH4 derivative

<400> SEQUENCE: 44

Lys Lys Ala Leu Leu His Leu Ala Leu Leu His Ala Ala Leu Leu Ala
1               5                   10                  15

His Leu Ala Ala Leu His Leu Lys Lys Ala
            20                  25

<210> SEQ ID NO 45
<211> LENGTH: 26
<212> TYPE: PRT
<213> ORGANISM: artificial
<220> FEATURE:
<223> OTHER INFORMATION: Synthetic LAH4 derivative

<400> SEQUENCE: 45

Lys Lys Ala Leu Leu His Leu Ala Leu Leu Leu Ala Ala Leu His Ala
1               5                   10                  15

His Leu Ala Ala Leu His Leu Lys Lys Ala
            20                  25

<210> SEQ ID NO 46
<211> LENGTH: 26
<212> TYPE: PRT
<213> ORGANISM: artificial
<220> FEATURE:
<223> OTHER INFORMATION: Synthetic LAH4 derivative

<400> SEQUENCE: 46

Lys Lys Ala Leu Leu Ala His Ala Leu His Leu Leu Ala Ala Leu Ala
1               5                   10                  15

Leu His Leu Ala His Leu Leu Lys Lys Ala
            20                  25

<210> SEQ ID NO 47
<211> LENGTH: 26
<212> TYPE: PRT
<213> ORGANISM: artificial
<220> FEATURE:
<223> OTHER INFORMATION: Synthetic LAH4 derivative

<400> SEQUENCE: 47

Lys Lys Ala Leu Leu Leu Ala Ala Leu His His Leu Ala Ala Leu Ala
1               5                   10                  15

Leu His Leu Ala His Leu Leu Lys Lys Ala
            20                  25

<210> SEQ ID NO 48
<211> LENGTH: 26
<212> TYPE: PRT
<213> ORGANISM: artificial
<220> FEATURE:
<223> OTHER INFORMATION: Synthetic LAH4 derivative

<400> SEQUENCE: 48

Lys Lys Ala Leu Leu Leu Ala Ala Leu His His Leu Leu Ala Leu Ala
1               5                   10                  15

His His Leu Ala Ala Leu Leu Lys Lys Ala
            20                  25

-continued

<210> SEQ ID NO 49
<211> LENGTH: 26
<212> TYPE: PRT
<213> ORGANISM: artificial
<220> FEATURE:
<223> OTHER INFORMATION: Synthetic LAH4 derivative

<400> SEQUENCE: 49

Lys Lys Ala Leu Leu His Ala Ala Leu Ala His Leu Leu Ala Leu Ala
1               5                   10                  15

His His Leu Leu Ala Leu Leu Lys Lys Ala
            20                  25

<210> SEQ ID NO 50
<211> LENGTH: 26
<212> TYPE: PRT
<213> ORGANISM: artificial
<220> FEATURE:
<223> OTHER INFORMATION: Synthetic LAH4 derivative

<400> SEQUENCE: 50

Lys Lys Ala Leu Leu His Ala Leu Leu Ala His Leu Ala Ala Leu Leu
1               5                   10                  15

His Ala Leu Leu Ala His Leu Lys Lys Ala
            20                  25

<210> SEQ ID NO 51
<211> LENGTH: 26
<212> TYPE: PRT
<213> ORGANISM: artificial
<220> FEATURE:
<223> OTHER INFORMATION: Synthetic LAH4 derivative

<400> SEQUENCE: 51

Lys Lys Ala Leu Leu His Ala Leu Leu Ala Ala Leu Leu Ala His Leu
1               5                   10                  15

His Ala Leu Leu Ala His Leu Lys Lys Ala
            20                  25

<210> SEQ ID NO 52
<211> LENGTH: 25
<212> TYPE: PRT
<213> ORGANISM: artificial
<220> FEATURE:
<223> OTHER INFORMATION: Synthetic LAH4 derivative

<400> SEQUENCE: 52

Lys Ala Leu Leu His Ala Ala Leu Ala His Leu Leu Ala Leu Ala His
1               5                   10                  15

His Leu Leu Ala Leu Leu Lys Lys Ala
            20                  25

<210> SEQ ID NO 53
<211> LENGTH: 26
<212> TYPE: PRT
<213> ORGANISM: artificial
<220> FEATURE:
<223> OTHER INFORMATION: Synthetic LAH4 derivative

<400> SEQUENCE: 53

Lys Lys Lys Leu Leu His Ala Ala Leu Ala His Leu Leu Ala Leu Ala
1               5                   10                  15

His His Leu Leu Ala Leu Leu Lys Lys Ala

```
            20                  25

<210> SEQ ID NO 54
<211> LENGTH: 24
<212> TYPE: PRT
<213> ORGANISM: artificial
<220> FEATURE:
<223> OTHER INFORMATION: Synthetic LAH4 derivative

<400> SEQUENCE: 54

Lys Lys Ala Leu Leu His Ala Ala Leu Ala His Leu Leu Ala Leu Ala
1               5                   10                  15

His His Leu Leu Ala Leu Leu Ala
            20

<210> SEQ ID NO 55
<211> LENGTH: 25
<212> TYPE: PRT
<213> ORGANISM: artificial
<220> FEATURE:
<223> OTHER INFORMATION: Synthetic LAH4 derivative

<400> SEQUENCE: 55

Lys Lys Ala Leu Leu His Ala Ala Leu Ala His Leu Leu Ala Leu Ala
1               5                   10                  15

His His Leu Leu Ala Leu Leu Lys Lys
            20                  25

<210> SEQ ID NO 56
<211> LENGTH: 24
<212> TYPE: PRT
<213> ORGANISM: artificial
<220> FEATURE:
<223> OTHER INFORMATION: Synthetic LAH4 derivative

<400> SEQUENCE: 56

Lys Lys Leu Leu His Ala Ala Leu Ala His Leu Leu Ala Leu Ala His
1               5                   10                  15

His Leu Leu Ala Leu Leu Lys Lys
            20

<210> SEQ ID NO 57
<211> LENGTH: 24
<212> TYPE: PRT
<213> ORGANISM: artificial
<220> FEATURE:
<223> OTHER INFORMATION: Synthetic LAH4 derivative

<400> SEQUENCE: 57

Lys Lys Ala Leu Leu His Ala Ala Leu Ala His Leu Leu Ala Leu Ala
1               5                   10                  15

His His Leu Leu Ala Leu Lys Lys
            20

<210> SEQ ID NO 58
<211> LENGTH: 23
<212> TYPE: PRT
<213> ORGANISM: artificial
<220> FEATURE:
<223> OTHER INFORMATION: Synthetic LAH4 derivative

<400> SEQUENCE: 58

Lys Lys Leu His Ala Ala Leu Ala His Leu Leu Ala Leu Ala His His
1               5                   10                  15
```

Leu Leu Ala Leu Leu Lys Lys
            20

<210> SEQ ID NO 59
<211> LENGTH: 21
<212> TYPE: PRT
<213> ORGANISM: artificial
<220> FEATURE:
<223> OTHER INFORMATION: Synthetic LAH4 derivative

<400> SEQUENCE: 59

Lys Lys Leu His Ala Ala Leu Ala His Leu Leu Ala Leu Ala His His
1               5                   10                  15

Leu Leu Ala Lys Lys
            20

<210> SEQ ID NO 60
<211> LENGTH: 26
<212> TYPE: PRT
<213> ORGANISM: artificial
<220> FEATURE:
<223> OTHER INFORMATION: Synthetic LAH4 derivative

<400> SEQUENCE: 60

Lys Lys Ala Leu Leu His Ala Ala Leu Ala His Leu Leu Ala Leu Ala
1               5                   10                  15

Ala Ala Leu Leu Ala Leu Leu Lys Lys Ala
            20                  25

<210> SEQ ID NO 61
<211> LENGTH: 26
<212> TYPE: PRT
<213> ORGANISM: artificial
<220> FEATURE:
<223> OTHER INFORMATION: Synthetic LAH4 derivative

<400> SEQUENCE: 61

Lys Lys Ala Leu Leu Ala Ala Ala Leu Ala Ala Leu Leu Ala Leu Ala
1               5                   10                  15

Ala Ala Leu Leu Ala Leu Leu Lys Lys Ala
            20                  25

<210> SEQ ID NO 62
<211> LENGTH: 26
<212> TYPE: PRT
<213> ORGANISM: artificial
<220> FEATURE:
<223> OTHER INFORMATION: Synthetic LAH4 derivative

<400> SEQUENCE: 62

Lys Lys Leu Leu Leu His Ala Leu Leu Ala His Leu Leu Ala Leu Leu
1               5                   10                  15

His His Leu Leu Ala Leu Leu Lys Lys Leu
            20                  25

<210> SEQ ID NO 63
<211> LENGTH: 450
<212> TYPE: PRT
<213> ORGANISM: Homo sapiens

<400> SEQUENCE: 63

Met Glu Gly Ser Lys Thr Ser Asn Asn Ser Thr Met Gln Val Ser Phe
1               5                   10                  15

Val Cys Gln Arg Cys Ser Gln Pro Leu Lys Leu Asp Thr Ser Phe Lys

```
            20                  25                  30
Ile Leu Asp Arg Val Thr Ile Gln Glu Leu Thr Ala Pro Leu Leu Thr
            35                  40                  45

Thr Ala Gln Ala Lys Pro Gly Glu Thr Gln Glu Glu Thr Asn Ser
    50                  55                  60

Gly Glu Glu Pro Phe Ile Glu Thr Pro Arg Gln Asp Gly Val Ser Arg
65                  70                  75                  80

Arg Phe Ile Pro Pro Ala Arg Met Met Ser Thr Glu Ser Ala Asn Ser
                85                  90                  95

Phe Thr Leu Ile Gly Glu Ala Ser Asp Gly Thr Met Glu Asn Leu
            100                 105                 110

Ser Arg Arg Leu Lys Val Thr Gly Asp Leu Phe Asp Ile Met Ser Gly
        115                 120                 125

Gln Thr Asp Val Asp His Pro Leu Cys Glu Glu Cys Thr Asp Thr Leu
        130                 135                 140

Leu Asp Gln Leu Asp Thr Gln Leu Asn Val Thr Glu Asn Glu Cys Gln
145                 150                 155                 160

Asn Tyr Lys Arg Cys Leu Glu Ile Leu Glu Gln Met Asn Glu Asp Asp
                165                 170                 175

Ser Glu Gln Leu Gln Met Glu Leu Lys Glu Leu Ala Leu Glu Glu Glu
            180                 185                 190

Arg Leu Ile Gln Glu Leu Glu Asp Val Glu Lys Asn Arg Lys Ile Val
        195                 200                 205

Ala Glu Asn Leu Glu Lys Val Gln Ala Glu Ala Glu Arg Leu Asp Gln
        210                 215                 220

Glu Glu Ala Gln Tyr Gln Arg Glu Tyr Ser Glu Phe Lys Arg Gln Gln
225                 230                 235                 240

Leu Glu Leu Asp Asp Glu Leu Lys Ser Val Glu Asn Gln Met Arg Tyr
                245                 250                 255

Ala Gln Thr Gln Leu Asp Lys Leu Lys Lys Thr Asn Val Phe Asn Ala
            260                 265                 270

Thr Phe His Ile Trp His Ser Gly Gln Phe Gly Thr Ile Asn Asn Phe
        275                 280                 285

Arg Leu Gly Arg Leu Pro Ser Val Pro Val Glu Trp Asn Glu Ile Asn
        290                 295                 300

Ala Ala Trp Gly Gln Thr Val Leu Leu His Ala Leu Ala Asn Lys
305                 310                 315                 320

Met Gly Leu Lys Phe Gln Arg Tyr Arg Leu Val Pro Tyr Gly Asn His
                325                 330                 335

Ser Tyr Leu Glu Ser Leu Thr Asp Lys Ser Lys Glu Leu Pro Leu Tyr
            340                 345                 350

Cys Ser Gly Gly Leu Arg Phe Phe Trp Asp Asn Lys Phe Asp His Ala
        355                 360                 365

Met Val Ala Phe Leu Asp Cys Val Gln Gln Phe Lys Glu Glu Val Glu
        370                 375                 380

Lys Gly Glu Thr Arg Phe Cys Leu Pro Tyr Arg Met Asp Val Glu Lys
385                 390                 395                 400

Gly Lys Ile Glu Asp Thr Gly Ser Gly Ser Tyr Ser Ile Lys
                405                 410                 415

Thr Gln Phe Asn Ser Glu Glu Gln Trp Thr Lys Ala Leu Lys Phe Met
            420                 425                 430

Leu Thr Asn Leu Lys Trp Gly Leu Ala Trp Val Ser Ser Gln Phe Tyr
        435                 440                 445
```

Asn Lys
    450

<210> SEQ ID NO 64
<211> LENGTH: 431
<212> TYPE: PRT
<213> ORGANISM: Homo sapiens

<400> SEQUENCE: 64

Met Ser Ser Ile Arg Phe Leu Cys Gln Arg Cys His Gln Ala Leu Lys
1               5                   10                  15

Leu Ser Gly Ser Ser Glu Ser Arg Ser Leu Pro Ala Ala Pro Ala Pro
            20                  25                  30

Thr Ser Gly Gln Ala Glu Pro Gly Asp Thr Arg Glu Pro Gly Val Thr
        35                  40                  45

Thr Arg Glu Val Thr Asp Ala Glu Glu Gln Gln Asp Gly Ala Ser Ser
    50                  55                  60

Arg Ser Pro Pro Gly Asp Gly Ser Val Ser Lys Gly His Ala Asn Ile
65                  70                  75                  80

Phe Thr Leu Leu Gly Glu Leu Gly Ala Met His Met Leu Ser Ser Ile
                85                  90                  95

Gln Lys Ala Ala Gly Asp Ile Phe Asp Ile Val Ser Gly Gln Ala Val
            100                 105                 110

Val Asp His Pro Leu Cys Glu Glu Cys Thr Asp Ser Leu Leu Glu Gln
        115                 120                 125

Leu Asp Ile Gln Leu Ala Leu Thr Glu Ala Asp Ser Gln Asn Tyr Gln
    130                 135                 140

Arg Cys Leu Glu Thr Gly Glu Leu Ala Thr Ser Glu Asp Glu Ala Ala
145                 150                 155                 160

Ala Leu Arg Ala Glu Leu Arg Asp Leu Glu Leu Glu Ala Arg Leu
                165                 170                 175

Val Gln Glu Leu Glu Asp Val Asp Arg Asn Asn Ala Arg Ala Ala Ala
            180                 185                 190

Asp Leu Gln Ala Ala Gln Ala Glu Ala Ala Glu Leu Asp Gln Gln Glu
        195                 200                 205

Arg Gln His Tyr Arg Asp Tyr Ser Ala Leu Lys Arg Gln Gln Leu Glu
    210                 215                 220

Leu Leu Asp Gln Leu Gly Asn Val Glu Asn Gln Leu Gln Tyr Ala Arg
225                 230                 235                 240

Val Gln Arg Asp Arg Leu Lys Glu Ile Asn Cys Phe Thr Ala Thr Phe
                245                 250                 255

Glu Ile Trp Val Glu Gly Pro Leu Gly Val Ile Asn Asn Phe Arg Leu
            260                 265                 270

Gly Arg Leu Pro Thr Val Arg Val Gly Trp Asn Glu Ile Asn Thr Ala
        275                 280                 285

Trp Gly Gln Ala Leu Leu Leu Leu Thr Leu Ala Asn Thr Ile Gly
    290                 295                 300

Leu Gln Phe Gln Arg Tyr Arg Leu Ile Pro Cys Gly Asn His Ser Tyr
305                 310                 315                 320

Leu Lys Ser Leu Thr Asp Arg Thr Glu Leu Pro Leu Phe Cys Tyr
                325                 330                 335

Gly Gly Gln Asp Val Phe Leu Asn Asn Lys Tyr Asp Arg Ala Met Val
            340                 345                 350

Ala Phe Leu Asp Cys Met Gln Gln Phe Lys Glu Glu Ala Glu Lys Gly

```
                    355                 360                 365

Glu Leu Gly Leu Ser Leu Pro Tyr Gly Ile Gln Val Glu Thr Gly Leu
                370                 375                 380

Met Glu Asp Val Gly Gly Arg Gly Glu Cys Tyr Ser Ile Arg Thr His
385                 390                 395                 400

Leu Asn Thr Gln Glu Leu Trp Thr Lys Ala Leu Lys Phe Met Leu Ile
                405                 410                 415

Asn Phe Lys Trp Ser Leu Ile Trp Val Ala Ser Arg Tyr Gln Lys
                420                 425                 430

<210> SEQ ID NO 65
<211> LENGTH: 18
<212> TYPE: PRT
<213> ORGANISM: artificial
<220> FEATURE:
<223> OTHER INFORMATION: Synthetic beclin-1 267-284

<400> SEQUENCE: 65

Thr Asn Val Phe Asn Ala Thr Phe His Ile Trp His Ser Gly Gln Phe
1               5                   10                  15

Gly Thr

<210> SEQ ID NO 66
<211> LENGTH: 18
<212> TYPE: PRT
<213> ORGANISM: artificial
<220> FEATURE:
<223> OTHER INFORMATION: Synthetic modified beclin-1 267-284

<400> SEQUENCE: 66

Thr Asn Val Phe Asn Ala Thr Phe Glu Ile Trp His Asp Gly Glu Phe
1               5                   10                  15

Gly Thr

<210> SEQ ID NO 67
<211> LENGTH: 15
<212> TYPE: PRT
<213> ORGANISM: artificial
<220> FEATURE:
<223> OTHER INFORMATION: Synthetic modified beclin-1 270-284

<400> SEQUENCE: 67

Phe Asn Ala Thr Phe Glu Ile Trp His Asp Gly Glu Phe Gly Thr
1               5                   10                  15

<210> SEQ ID NO 68
<211> LENGTH: 16
<212> TYPE: PRT
<213> ORGANISM: artificial
<220> FEATURE:
<223> OTHER INFORMATION: Synthetic modified beclin-1 267-282

<400> SEQUENCE: 68

Thr Asn Val Phe Asn Ala Thr Phe Glu Ile Trp His Asp Gly Glu Phe
1               5                   10                  15

<210> SEQ ID NO 69
<211> LENGTH: 29
<212> TYPE: PRT
<213> ORGANISM: artificial
<220> FEATURE:
<223> OTHER INFORMATION: Synthetic modified beclin-1 256-284

<400> SEQUENCE: 69
```

Tyr Ala Gln Thr Gln Leu Asp Lys Leu Lys Lys Thr Asn Val Phe Asn
1               5                   10                  15

Ala Thr Phe Glu Ile Trp His Asp Gly Glu Phe Gly Thr
            20                  25

<210> SEQ ID NO 70
<211> LENGTH: 30
<212> TYPE: PRT
<213> ORGANISM: artificial
<220> FEATURE:
<223> OTHER INFORMATION: Synthetic modified beclin-1 267-296

<400> SEQUENCE: 70

Thr Asn Val Phe Asn Ala Thr Phe Glu Ile Trp His Asp Gly Glu Phe
1               5                   10                  15

Gly Thr Ile Asn Asn Phe Arg Leu Gly Arg Leu Pro Ser Val
            20                  25                  30

<210> SEQ ID NO 71
<211> LENGTH: 33
<212> TYPE: PRT
<213> ORGANISM: artificial
<220> FEATURE:
<223> OTHER INFORMATION: Synthetic modified beclin-1 250-282

<400> SEQUENCE: 71

Val Glu Asn Gln Met Arg Tyr Ala Gln Thr Gln Leu Asp Lys Leu Lys
1               5                   10                  15

Lys Thr Asn Val Phe Asn Ala Thr Phe Glu Ile Trp His Asp Gly Glu
            20                  25                  30

Phe

<210> SEQ ID NO 72
<211> LENGTH: 29
<212> TYPE: PRT
<213> ORGANISM: artificial
<220> FEATURE:
<223> OTHER INFORMATION: Synthetic modified beclin-1 270-298

<400> SEQUENCE: 72

Phe Asn Ala Thr Phe Glu Ile Trp His Asp Gly Glu Phe Gly Thr Ile
1               5                   10                  15

Asn Asn Phe Arg Leu Gly Arg Leu Pro Ser Val Pro Val
            20                  25

<210> SEQ ID NO 73
<211> LENGTH: 25
<212> TYPE: PRT
<213> ORGANISM: artificial
<220> FEATURE:
<223> OTHER INFORMATION: Synthetic modified beclin-1 274-298

<400> SEQUENCE: 73

Phe Glu Ile Trp His Asp Gly Glu Phe Gly Thr Ile Asn Asn Phe Arg
1               5                   10                  15

Leu Gly Arg Leu Pro Ser Val Pro Val
            20                  25

<210> SEQ ID NO 74
<211> LENGTH: 41
<212> TYPE: PRT
<213> ORGANISM: artificial
<220> FEATURE:

<223> OTHER INFORMATION: Synthetic modified Tat-Beclin-1 + beclin-1
      285-296

<400> SEQUENCE: 74

Tyr Gly Arg Lys Lys Arg Arg Gln Arg Arg Thr Asn Val Phe Asn
1               5                   10                  15

Ala Thr Phe Glu Ile Trp His Asp Gly Glu Phe Gly Thr Ile Asn Asn
            20                  25                  30

Phe Arg Leu Gly Arg Leu Pro Ser Val
        35                  40

<210> SEQ ID NO 75
<211> LENGTH: 31
<212> TYPE: PRT
<213> ORGANISM: artificial
<220> FEATURE:
<223> OTHER INFORMATION: Synthetic TB1

<400> SEQUENCE: 75

Tyr Gly Arg Lys Lys Arg Arg Gln Arg Arg Gly Gly Thr Asn Val
1               5                   10                  15

Phe Asn Ala Thr Phe Glu Ile Trp His Asp Gly Glu Phe Gly Thr
            20                  25                  30

<210> SEQ ID NO 76
<211> LENGTH: 36
<212> TYPE: PRT
<213> ORGANISM: artificial
<220> FEATURE:
<223> OTHER INFORMATION: Synthetic MAP-B1

<400> SEQUENCE: 76

Lys Leu Ala Leu Lys Leu Ala Leu Lys Ala Leu Lys Ala Ala Leu Lys
1               5                   10                  15

Ala Gly Thr Asn Val Phe Asn Ala Thr Phe Glu Ile Trp His Asp Gly
            20                  25                  30

Glu Phe Gly Thr
        35

<210> SEQ ID NO 77
<211> LENGTH: 31
<212> TYPE: PRT
<213> ORGANISM: artificial
<220> FEATURE:
<223> OTHER INFORMATION: Synthetic TB WT

<400> SEQUENCE: 77

Tyr Gly Arg Lys Lys Arg Arg Gln Arg Arg Gly Gly Thr Asn Val
1               5                   10                  15

Phe Asn Ala Thr Phe His Ile Trp His Ser Gly Gln Phe Gly Thr
            20                  25                  30

<210> SEQ ID NO 78
<211> LENGTH: 42
<212> TYPE: PRT
<213> ORGANISM: artificial
<220> FEATURE:
<223> OTHER INFORMATION: Synthetic TB1 256-284

<400> SEQUENCE: 78

Tyr Gly Arg Lys Lys Arg Arg Gln Arg Arg Gly Gly Tyr Ala Gln
1               5                   10                  15

Thr Gln Leu Asp Lys Leu Lys Lys Thr Asn Val Phe Asn Ala Thr Phe

```
                    20                  25                  30

Glu Ile Trp His Asp Gly Glu Phe Gly Thr
            35                  40

<210> SEQ ID NO 79
<211> LENGTH: 43
<212> TYPE: PRT
<213> ORGANISM: artificial
<220> FEATURE:
<223> OTHER INFORMATION: Synthetic TB1 267-296

<400> SEQUENCE: 79

Tyr Gly Arg Lys Lys Arg Arg Gln Arg Arg Gly Gly Thr Asn Val
1               5                   10                  15

Phe Asn Ala Thr Phe Glu Ile Trp His Asp Gly Glu Phe Gly Thr Ile
            20                  25                  30

Asn Asn Phe Arg Leu Gly Arg Leu Pro Ser Val
            35                  40

<210> SEQ ID NO 80
<211> LENGTH: 43
<212> TYPE: PRT
<213> ORGANISM: artificial
<220> FEATURE:
<223> OTHER INFORMATION: Synthetic TB WT 267-296

<400> SEQUENCE: 80

Tyr Gly Arg Lys Lys Arg Arg Gln Arg Arg Gly Gly Thr Asn Val
1               5                   10                  15

Phe Asn Ala Thr Phe His Ile Trp His Ser Gly Gln Phe Gly Thr Ile
            20                  25                  30

Asn Asn Phe Arg Leu Gly Arg Leu Pro Ser Val
            35                  40

<210> SEQ ID NO 81
<211> LENGTH: 46
<212> TYPE: PRT
<213> ORGANISM: artificial
<220> FEATURE:
<223> OTHER INFORMATION: Synthetic TB1 250-282

<400> SEQUENCE: 81

Tyr Gly Arg Lys Lys Arg Arg Gln Arg Arg Gly Gly Val Glu Asn
1               5                   10                  15

Gln Met Arg Tyr Ala Gln Thr Gln Leu Asp Lys Leu Lys Lys Thr Asn
            20                  25                  30

Val Phe Asn Ala Thr Phe Glu Ile Trp His Asp Gly Glu Phe
            35                  40                  45

<210> SEQ ID NO 82
<211> LENGTH: 38
<212> TYPE: PRT
<213> ORGANISM: artificial
<220> FEATURE:
<223> OTHER INFORMATION: Synthetic TB1 274-298

<400> SEQUENCE: 82

Tyr Gly Arg Lys Lys Arg Arg Gln Arg Arg Gly Gly Phe Glu Ile
1               5                   10                  15

Trp His Asp Gly Glu Phe Gly Thr Ile Asn Asn Phe Arg Leu Gly Arg
            20                  25                  30

Leu Pro Ser Val Pro Val
```

<210> SEQ ID NO 83
<211> LENGTH: 42
<212> TYPE: PRT
<213> ORGANISM: artificial
<220> FEATURE:
<223> OTHER INFORMATION: Synthetic TB1 270-298

<400> SEQUENCE: 83

Tyr Gly Arg Lys Lys Arg Arg Gln Arg Arg Gly Gly Phe Asn Ala
1               5                   10                  15

Thr Phe Glu Ile Trp His Asp Gly Glu Phe Gly Thr Ile Asn Asn Phe
            20                  25                  30

Arg Leu Gly Arg Leu Pro Ser Val Pro Val
        35                  40

<210> SEQ ID NO 84
<211> LENGTH: 26
<212> TYPE: PRT
<213> ORGANISM: artificial
<220> FEATURE:
<223> OTHER INFORMATION: Synthetic vectofusin-1

<400> SEQUENCE: 84

Lys Lys Ala Leu Leu His Ala Ala Leu Ala His Leu Leu Ala Leu Ala
1               5                   10                  15

His His Leu Leu Ala Leu Leu Lys Lys Ala
20 25

<210> SEQ ID NO 85
<211> LENGTH: 39
<212> TYPE: PRT
<213> ORGANISM: artificial
<220> FEATURE:
<223> OTHER INFORMATION: Synthetic SEVI

<400> SEQUENCE: 85

Gly Ile His Lys Gln Lys Glu Lys Ser Arg Leu Gln Gly Gly Val Leu
1 5 10 15

Val Asn Glu Ile Leu Asn His Met Lys Arg Ala Thr Gln Ile Pro Ser
20 25 30

Tyr Lys Lys Leu Ile Met Tyr
35

<210> SEQ ID NO 86
<211> LENGTH: 22
<212> TYPE: PRT
<213> ORGANISM: artificial
<220> FEATURE:
<223> OTHER INFORMATION: Synthetic SEM1(86-107)

<400> SEQUENCE: 86

Asp Leu Asn Ala Leu His Lys Thr Thr Lys Ser Gln Arg His Leu Gly
1 5 10 15

Gly Ser Gln Gln Leu Leu
20

<210> SEQ ID NO 87
<211> LENGTH: 12
<212> TYPE: PRT
<213> ORGANISM: artificial
<220> FEATURE:
<223> OTHER INFORMATION: Synthetic EF-C peptide -continued

<400> SEQUENCE: 87

Gln Cys Lys Ile Lys Gln Ile Ile Asn Met Trp Gln
1               5                   10

<210> SEQ ID NO 88
<211> LENGTH: 16
<212> TYPE: PRT
<213> ORGANISM: artificial
<220> FEATURE:
<223> OTHER INFORMATION: Synthetic P16 peptide

<400> SEQUENCE: 88

Asn Trp Phe Asp Ile Thr Asn Trp Leu Trp Tyr Ile Lys Lys Lys Lys
1               5                   10                  15

<210> SEQ ID NO 89
<211> LENGTH: 18
<212> TYPE: PRT
<213> ORGANISM: artificial
<220> FEATURE:
<223> OTHER INFORMATION: Synthetic Beclin-2 249-266

<400> SEQUENCE: 89

Ile Asn Cys Phe Thr Ala Thr Phe Glu Ile Trp Val Glu Gly Pro Leu
1               5                   10                  15

Gly Val

<210> SEQ ID NO 90
<211> LENGTH: 29
<212> TYPE: PRT
<213> ORGANISM: artificial
<220> FEATURE:
<223> OTHER INFORMATION: Synthetic TAT+ beclin-2

<400> SEQUENCE: 90

Tyr Gly Arg Lys Lys Arg Arg Gln Arg Arg Ile Asn Cys Phe Thr
1               5                   10                  15

Ala Thr Phe Glu Ile Trp Val Glu Gly Pro Leu Gly Val
            20                  25

<210> SEQ ID NO 91
<211> LENGTH: 31
<212> TYPE: PRT
<213> ORGANISM: artificial
<220> FEATURE:
<223> OTHER INFORMATION: Synthetic TAT+ GG + Beclin2

<400> SEQUENCE: 91

Tyr Gly Arg Lys Lys Arg Arg Gln Arg Arg Gly Gly Ile Asn Cys
1               5                   10                  15

Phe Thr Ala Thr Phe Glu Ile Trp Val Glu Gly Pro Leu Gly Val
            20                  25                  30

<210> SEQ ID NO 92
<211> LENGTH: 18
<212> TYPE: PRT
<213> ORGANISM: artificial
<220> FEATURE:
<223> OTHER INFORMATION: Synthetic Mouse Beclin-2 262-279

<400> SEQUENCE: 92

Thr Asn Ile Phe Asn Ala Thr Phe Thr Ile Ser Asp Glu Gly Pro Leu
1               5                   10                  15

Gly Val

<210> SEQ ID NO 93
<211> LENGTH: 18
<212> TYPE: PRT
<213> ORGANISM: artificial
<220> FEATURE:
<223> OTHER INFORMATION: Synthetic Horse Beclin-2 253-270

<400> SEQUENCE: 93

Ile Asn Val Phe Ser Val Thr Phe Glu Ile Gly His Ser Gly Pro Val
1               5                   10                  15

Gly Val

<210> SEQ ID NO 94
<211> LENGTH: 18
<212> TYPE: PRT
<213> ORGANISM: artificial
<220> FEATURE:
<223> OTHER INFORMATION: Synthetic Panda Beclin-2 645-662

<400> SEQUENCE: 94

Thr Asn Val Phe Asn Ala Thr Phe Glu Ile Arg His Asp Gly Pro Val
1               5                   10                  15

Gly Ile

<210> SEQ ID NO 95
<211> LENGTH: 18
<212> TYPE: PRT
<213> ORGANISM: artificial
<220> FEATURE:
<223> OTHER INFORMATION: Synthetic Pig Beclin-2 244-261

<400> SEQUENCE: 95

Thr Asn Val Phe Arg Ala Thr Phe Glu Ile Arg His Ala Gly Pro Ile
1               5                   10                  15

Ala Ile

<210> SEQ ID NO 96
<211> LENGTH: 18
<212> TYPE: PRT
<213> ORGANISM: artificial
<220> FEATURE:
<223> OTHER INFORMATION: Synthetic Cow Beclin-2 248-265

<400> SEQUENCE: 96

Thr Asp Val Phe Asn Ala Thr Phe Glu Ile Trp Gln Asp Gly Pro Leu
1               5                   10                  15

Pro Val

<210> SEQ ID NO 97
<211> LENGTH: 18
<212> TYPE: PRT
<213> ORGANISM: artificial
<220> FEATURE:
<223> OTHER INFORMATION: Synthetic Rabbit Beclin-2 238-255

<400> SEQUENCE: 97

Thr Ser Ile Phe Gln Val Thr Phe Glu Ile Arg Glu Glu Gly Ser Val
1               5                   10                  15

Gly Ile

<210> SEQ ID NO 98

```
<211> LENGTH: 31
<212> TYPE: PRT
<213> ORGANISM: artificial
<220> FEATURE:
<223> OTHER INFORMATION: Synthetic tat-beclin1 H275E

<400> SEQUENCE: 98

Tyr Gly Arg Lys Lys Arg Arg Gln Arg Arg Gly Gly Thr Asn Val
1               5                   10                  15

Phe Asn Ala Thr Phe Glu Ile Trp His Ser Gly Gln Phe Gly Thr
            20                  25                  30

<210> SEQ ID NO 99
<211> LENGTH: 31
<212> TYPE: PRT
<213> ORGANISM: artificial
<220> FEATURE:
<223> OTHER INFORMATION: Synthetic tat-beclin 1 S279D

<400> SEQUENCE: 99

Tyr Gly Arg Lys Lys Arg Arg Gln Arg Arg Gly Gly Thr Asn Val
1               5                   10                  15

Phe Asn Ala Thr Phe His Ile Trp His Asp Gly Gln Phe Gly Thr
            20                  25                  30

<210> SEQ ID NO 100
<211> LENGTH: 31
<212> TYPE: PRT
<213> ORGANISM: artificial
<220> FEATURE:
<223> OTHER INFORMATION: Synthetic tat-beclin1 Q281E

<400> SEQUENCE: 100

Tyr Gly Arg Lys Lys Arg Arg Gln Arg Arg Gly Gly Thr Asn Val
1               5                   10                  15

Phe Asn Ala Thr Phe His Ile Trp His Ser Gly Glu Phe Gly Thr
            20                  25                  30

<210> SEQ ID NO 101
<211> LENGTH: 31
<212> TYPE: PRT
<213> ORGANISM: artificial
<220> FEATURE:
<223> OTHER INFORMATION: Synthetic tat-beclin1 F274 W277

<400> SEQUENCE: 101

Tyr Gly Arg Lys Lys Arg Arg Gln Arg Arg Gly Gly Thr Asn Val
1               5                   10                  15

Phe Asn Ala Thr Phe His Ile Trp His Ser Gly Gln Phe Gly Thr
            20                  25                  30

<210> SEQ ID NO 102
<211> LENGTH: 77
<212> TYPE: PRT
<213> ORGANISM: Homo sapiens

<400> SEQUENCE: 102

Glu Leu Lys Ser Val Glu Asn Gln Met Arg Tyr Ala Gln Thr Gln Leu
1               5                   10                  15

Asp Lys Leu Lys Lys Thr Asn Val Phe Asn Ala Thr Phe Glu Ile Trp
            20                  25                  30

His Asp Gly Glu Phe Gly Thr Ile Asn Asn Phe Arg Leu Gly Arg Leu
        35                  40                  45
```

-continued

```
Pro Ser Val Pro Val Glu Trp Asn Glu Ile Asn Ala Ala Trp Gly Gln
    50                  55                  60
Thr Val Leu Leu Leu His Ala Leu Ala Asn Lys Met Gly
65                  70                  75
```

COMPOSITIONS AND METHODS FOR IMPROVING VIRAL VECTOR EFFICIENCY

SEQUENCE LISTING

The instant application contains a Sequence Listing which has been submitted electronically in ASCII format and is hereby incorporated by reference in its entirety. Said ASCII copy, created on May 1, 2018, is named B2148_SL.txt and is 40,960 bytes in size.

FIELD OF THE INVENTION

The present invention relates to peptides and compositions for use in improving transduction efficiency of viruses into target cells.

BACKGROUND OF THE INVENTION

Gene therapy approaches are often hampered by low transduction efficiencies of target cells by recombinant viral vectors. Retroviral vectors, and in particular human immunodeficiency virus 1 (HIV-1)-based lentiviral vectors (LVs) are promising vehicles for gene therapy (D'Costa et al., 2009). These vectors are used currently in clinical applications to treat various diseases such as immune deficiencies, neurodegenerative or neurological diseases, anemias, HIV infection. Some of the applications of retroviral vectors rely on the transduction of specific target cells ex vivo such as hematopoietic stem/progenitor cells expressing the CD34 marker. A limiting factor with the use of recombinant lentiviral particles, is the capacity to obtain highly infectious titers during production of recombinant lentiviral vector particles. One way to circumvent this limitation is to concentrate the viral supernatant during the purification steps (Rodrigues et al., 2007). However, purification protocols are difficult to establish for some LVs, depending on the envelope glycoproteins used to pseudotype viral particles—as it is the case for GALVTR-LVs (LVs pseudotyped with gibbon ape leukemia virus envelope glycoprotein fused to the cytoplasmic tail of the amphotropic murine leukemia virus (MLV-A) envelope glycoprotein (Sandrin et al., 2002)). Therefore, many lentiviral vector preparations have low titer and transduction efficacy is limited. Another limiting factor is the ability of the lentiviral vector itself to infect target cells. Several envelope glycoproteins such as VSV-G, RD114TR, GALVTR can be used to pseudotype lentiviral vectors and have variable infectivity on target cells such as CD34+ cells (Sandrin et al., 2002). One strategy to circumvent these limitations is the addition of cofactors to optimize transduction protocols like cationic polymers (e.g. polybrene) or fibronectin fragments (e.g. retronectin) (Davis et al., 2004; Pollok et al., 1999). U.S. Pat. No. 7,759,467 describes a method for increasing the efficiency of transduction of hematopoietic cells by retroviruses comprising the infection of the cells in the presence of fibronectin or fibronectin fragments. However, the proposed method is not totally satisfactory for at least two reasons. First, the fragments of fibronectin used for improving the efficiency of retroviruses present significant economic drawbacks since they usually comprise around 270 or more amino acids. Furthermore, the use of fibronectin or fibronectin fragments requires coating of the culture plates and preloading of viral supernatants onto immobilized fibronectin fragments. These two steps are difficult to standardize and can lead to some saturation of target cell transduction depending on the concentrations of fibronectin fragments and viral supernatants used (Novelli et al., 1999).

Interestingly, natural cationic peptides called SEVI have been recently identified in human semen as strong enhancers of HIV-1 infectivity (Munch et al., 2007; Roan et al., 2009). This family of peptides has also been disclosed in international application No. PCT/EP2007/050727, which describes fragments of amino acid residues 240-290 of human prostatic acid phosphatase which promote viral infection of a cell.

The applicant has also previously proposed the use of the LAH4 peptide or a functional derivative thereof for promoting the infection of eukaryotic cells by a virus or viral vector in application No. PCT/EP2012/06264, which provided very good results, in particular in relation to the infection of hCD34+ cells with LV vectors.

The aim of the inventors was since to provide improved means for increasing transduction efficiency of a virus or viral vector into a target cell.

SUMMARY OF THE INVENTION

The present invention provides compositions and methods for improving virus transduction into a target cell.

The inventors have found that peptides comprising a cell-penetrating peptide (CPP) moiety and a Beclin-derived peptide moiety (both moieties being defined herein below), and in particular MAP-Beclin-1, Tat-Beclin-1 or Tat-Beclin-2 peptides have the property of promoting the transduction efficiency of viruses in eukaryotic cells. This observation is highly surprising because the Tat-Beclin 1 (TB1) peptide has previously been described as inducing autophagy, a cell mechanism involved in virus inhibition (WO2013/119377; Shoji-Kawata et al., 2013). Likewise, in 2013, He C. et al identified Beclin 2 (He C. et al, 2013) a mammalian-specific protein involved in autophagy, like Beclin 1. However, Beclin 2, but not Beclin 1, functions in an additional lysosomal degradation pathway. Yet, it is herein disclosed that peptides comprising a CPP moiety and a Beclin-derived peptide moiety, including Tat-Beclin 2 peptides, Tat-Beclin-1 peptides and MAP-Beclin-1 peptides, significantly improve transduction efficiency of a number of different virus types in different eukaryotic target cells.

Accordingly, in one aspect the present invention provides a method for promoting the infection of a cell by a virus, comprising contacting said cell with said virus and a peptide comprising:
(i) a CPP moiety; and
(ii) a Beclin-derived peptide moiety, in particular a Beclin-1- or Beclin-2-derived peptide moiety.

In a particular embodiment, the method of the invention is an in vitro method. More particularly, the method is implemented to increase the sensitivity of a cell-based assay for detecting the presence or absence of a virus in a sample. Indeed, thanks to the transduction enhancing properties of the peptide implemented in the present invention, even low amounts of viruses in a sample may be detected since their infectivity is improved.

In addition, the method of the invention may also be implemented for diagnosing an infection by a virus in a subject, comprising incubating a sample of the subject with a cell and a peptide according to the invention, comprising a CPP moiety and a Beclin-derived peptide moiety, in order to amplify the entry into said cell of any virus contained in said sample, and subsequently identifying the virus that has entered the cell.

More preferably, the present invention relates to the use of a peptide as defined above, including a CPP moiety and a Beclin-derived peptide moiety (e.g. a Beclin-1- or Beclin-2-derived peptide moiety), in a method for gene therapy in combination with a viral vector encoding a therapeutic gene.

In a particular embodiment, the virus or viral vector used with the peptide of the invention is a retrovirus, in particular a lentivirus, for example a pseudotyped lentivirus. In another embodiment, the virus or viral vector is a parvovirus, in particular an adeno-associated virus (AAV). In a particular embodiment, the peptide of the invention promotes the infection of a cell by a virus, wherein the cell is a hematopoietic stem/progenitor cell, preferably a hCD34+ cell. The peptide of the invention may also be used with another viral transduction enhancer, such as vectofusin, human fibronectin fragments, various semen-derived enhancers of viral infection or peptides derived from HIV-1 envelope glycoproteins.

Furthermore, the present invention relates to a peptide comprising a CPP moiety and a Beclin-derived peptide moiety (e.g. a Beclin-1- or Beclin-2-derived peptide moiety). In particular, the present invention relates to a peptide comprising a MAP moiety and a Beclin-1-derived peptide moiety.

Another aspect of the invention relates to a complex of a virus or viral vector with a peptide comprising a cell-penetrating peptide (CPP) moiety and a Beclin-derived peptide moiety. In another aspect, the invention relates to a mixture of a virus or viral vector with a peptide comprising a cell-penetrating peptide (CPP) moiety and a Beclin-derived peptide moiety. In a particular embodiment, the virus or viral vector in the complex or mixture of the invention is a retrovirus, in particular a lentivirus. Particular lentiviruses includes pseudotyped lentiviruses. In another embodiment, the virus or viral vector is a parvovirus, in particular an adeno-associated virus (AAV). In a further embodiment, the peptide is as defined above, and more specifically in the claims, or the peptide comprises or consists of the sequence shown in SEQ ID NO:75, SEQ ID NO:77 and SEQ ID NO:98-101.

The invention further relates to a nucleic acid construct comprising a polynucleotide encoding the peptide of the invention.

Another aspect of the invention relates to a kit comprising the peptide of the invention and a viral vector.

Other aspects and embodiments will be apparent from the following detailed description.

LEGENDS OF THE FIGURES

FIG. 1. Tat-Beclin1 promotes cell line transduction with various lentiviral vectors. A) HCT116 cells were transduced six hours with VSV-G-LVs ($2\times10^5$ TU/ml) in absence or presence of the indicated concentrations of Tat-Scrambled or Tat-Beclin1 peptide. B) HCT116 cells were transduced with various titers of VSV-G-LVs in absence or presence of Tat-Scrambled or Tat-Beclin1 peptide (5 µM). C) HCT116 cells were transduced with GALVTR-LVs or RD114TR-LVs ($10^6$ TU/ml) in absence or presence of Tat-Scrambled (5 µM), Tat-Beclin1 (5 µM), Vectofusin-1 (6 µg/ml), protamine sulfate (4 µg/ml) or polybrene (3 µg/ml). In the three panels, transduction efficiencies were evaluated after three to four days by monitoring GFP expression. All the data are expressed as the average of three independent experiments performed in duplicate ±standard error means (SEM).

Figure 2:
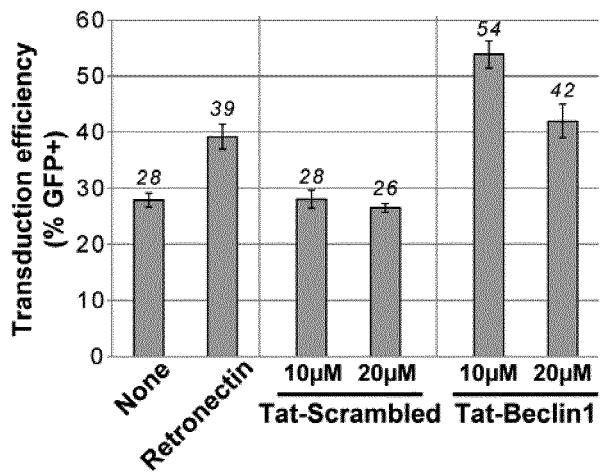
Figure 2:
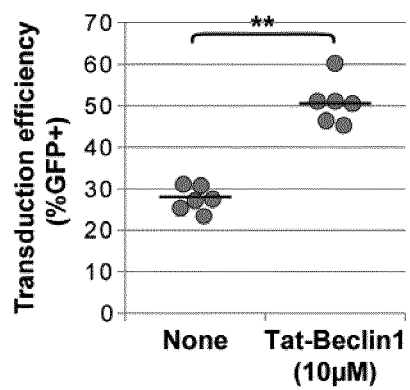
Figure 2:
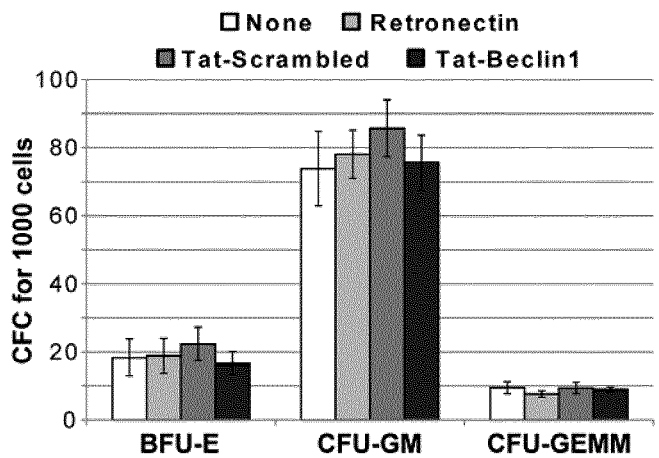

FIG. 2. Tat-Beclin1 enhances lentiviral transduction of hCD34+ HSPCs with no apparent cytotoxicity. A) hCD34+ cells were infected with highly purified VSV-G-LVs ($2\times10^7$ ig/ml, MOI 240) in the absence (none) or presence of Retronectin (7 µg/cm$^2$) or the indicated concentrations of Tat-Scrambled or Tat-Beclin1 peptide. After three to five days, transduction efficiencies were evaluated by monitoring GFP expression. Data are expressed as the average of three independent experiments (three UCB donors) performed in duplicate ±SEM. B) hCD34+ cells (six UCB donors) were transduced in duplicate with VSV-G-LVs ($2\times10^5$ TU/ml) in absence or presence of Tat-Beclin1 (10 µM). Data are represented as the average level of transduction for each UCB donors. Bars indicate the mean value of the distributions. The P-value was determined using the Mann-Whitney Test (**P<0.01). C) Differentiation of transduced hCD34+ cells in colony-forming cell (CFC) assay. Results represent the average number of different types of colonies obtained for 1000 cells plated after transduction with VSV-G-LVs ($5\times10^7$ ig/ml) in absence (none) or presence of Retronectin (7 µg/cm$^2$), Tat-Scrambled (10 µM) or Tat-Beclin1 (10 µM) peptide. Data are the average of three independent experiments (three UCB donors) performed in duplicate ±SEM.

Figure 3:
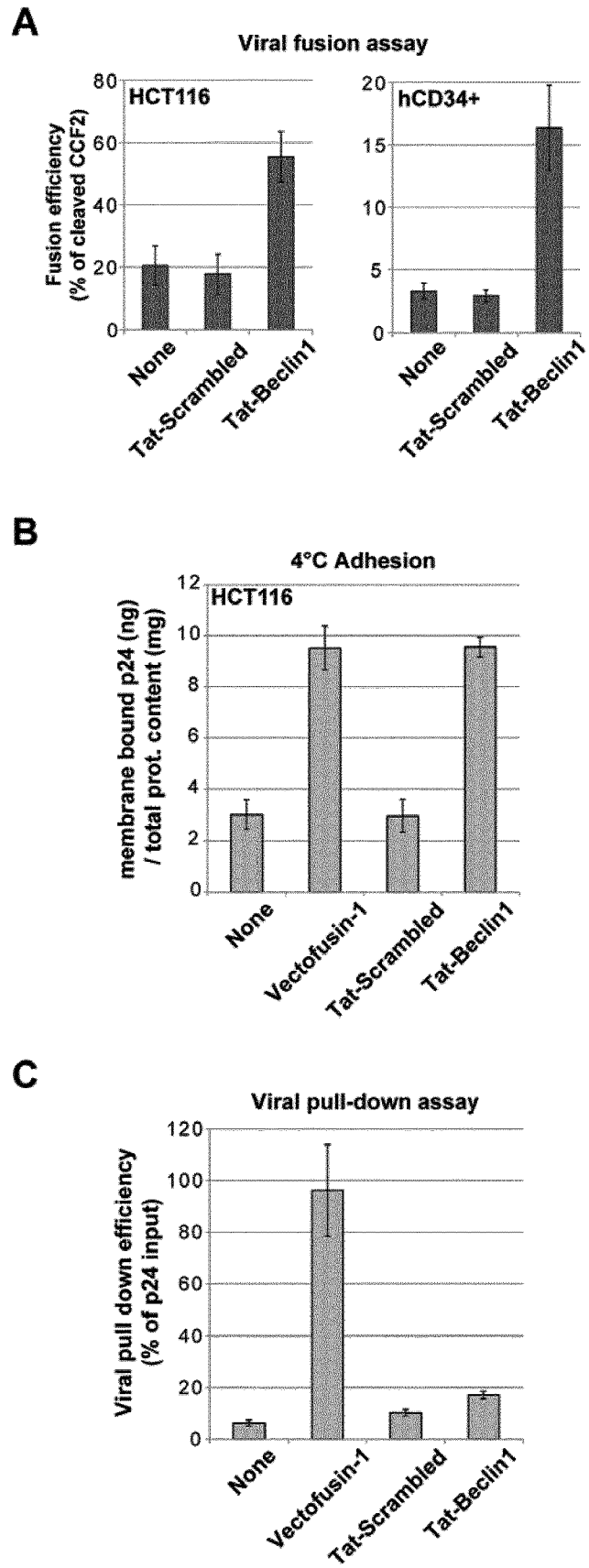

FIG. 3. Tat-Beclin1 promotes the adhesion and fusion of lentiviral particles with target cells. A) Viral fusion assay. Cells were incubated 2.5 hr at 37° C. with VSV-G-BLAM-LVs in absence (none) or presence of Tat-Scrambled or Tat-Beclin1 at 10 µM. Next, the viral fusion efficiency was estimated by monitoring the percentage of cleaved CCF2 substrate in the target cells using flow cytometry. Data are represented as the average of three independent experiments (three UCB donors for hCD34+ cells) performed in duplicate ±SEM. B) Adhesion assay. HCT116 cells were pre-incubated 30 min at 37° C. in absence or presence of Tat-Scrambled or Tat-Beclin1 (5 µM). Next, cells were incubated 2.5 hr at 4° C. with VSV-G-LVs (75 ng of p24) in absence or presence of Tat-Scrambled or Tat-Beclin1 (5 µM). As a positive control, one condition of HCT116 cells was incubated with a cold solution of VSV-G-LVs mixed with the aggregating peptide Vectofusin-1 (12 µg/ml). Data are represented as the average of three independent experiments performed in duplicate ±SEM. C) Viral pull-down assay. VSV-G-LV particles were mixed either with Tat-Scrambled (10 µM), Tat-Beclin1 (10 µM) or the positive control Vectofusin-1 (10 µM). After a short centrifugation (15,000 g), the percentage of pelleted viral particles was quantified using an HIV-1 p24 ELISA kit. Data are normalized to the level of p24 input and are represented as the average of three independent experiments performed in duplicate ±SEM.

Figure 4:
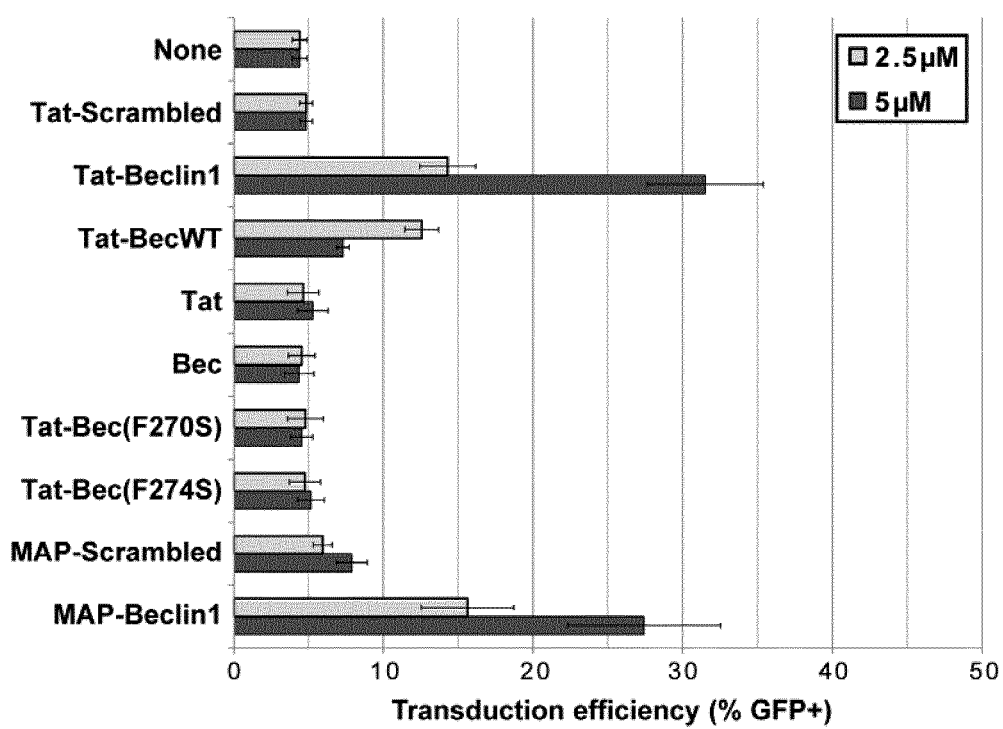

FIG. 4. Viral transduction enhancer activity of Tat-Beclin1 and various derivatives. HCT116 cells were transduced as described in FIG. 1A in absence (none) or presence of the indicated peptides either at 2.5 µM (light gray histogram) or 5 µM (black histogram). Data are expressed as the average of three independent experiments performed in duplicate ±SEM.

Figure 5:
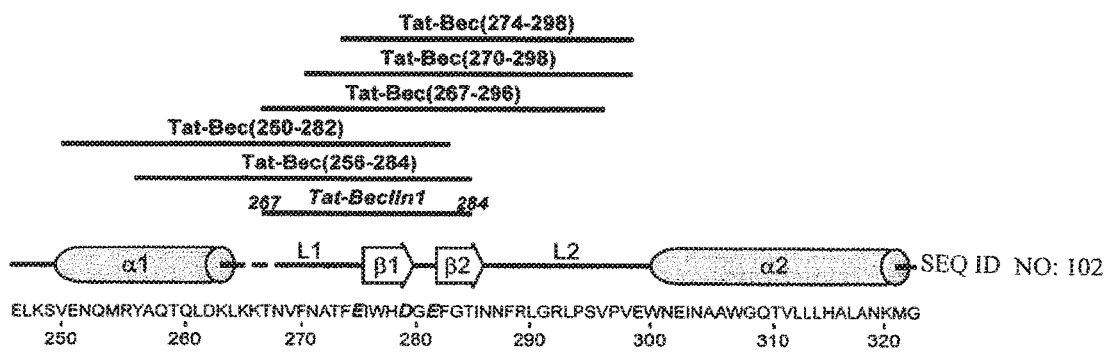
Figure 5:
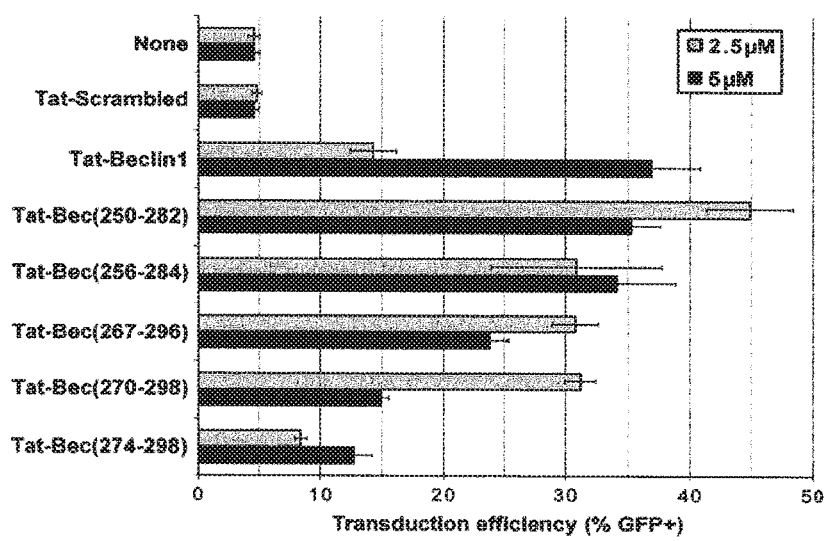
Figure 5:
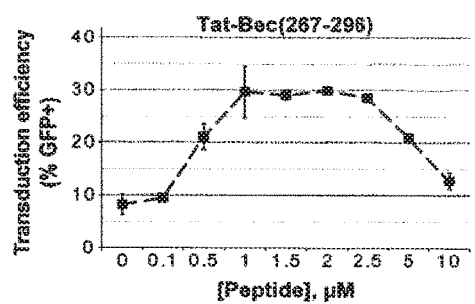
Figure 5:
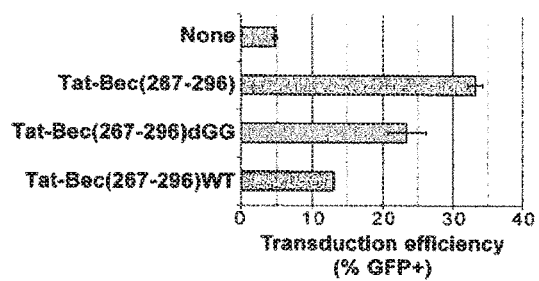

FIG. 5. Viral transduction efficiency of Tat-Beclin1 variants. A) Primary sequence of the human Beclin 1 protein from residue 246 to 322 (Homo sapiens, NP_003757). Mutations H275E, S279D and Q281E are highlighted in bold italic. Secondary structural elements are indicated above the sequence (alpha helix (α), Loop (L) and beta sheet (β)). Above the structural elements, dark lines represent the protein sequence coverage of each Tat-Beclin1 variants. B) HCT116 cells were transduced as described in FIG. 1A in absence (none) or presence of the indicated peptides either at 2.5 µM (light gray histogram) or 5 µM (black histogram) or C) with increasing concentrations of Tat-Bec(267-296) or D) with indicated peptides at 2.5 µM. For all the panels, data are expressed as the average of three independent experiments performed in duplicate ±SEM.

Figure 6:
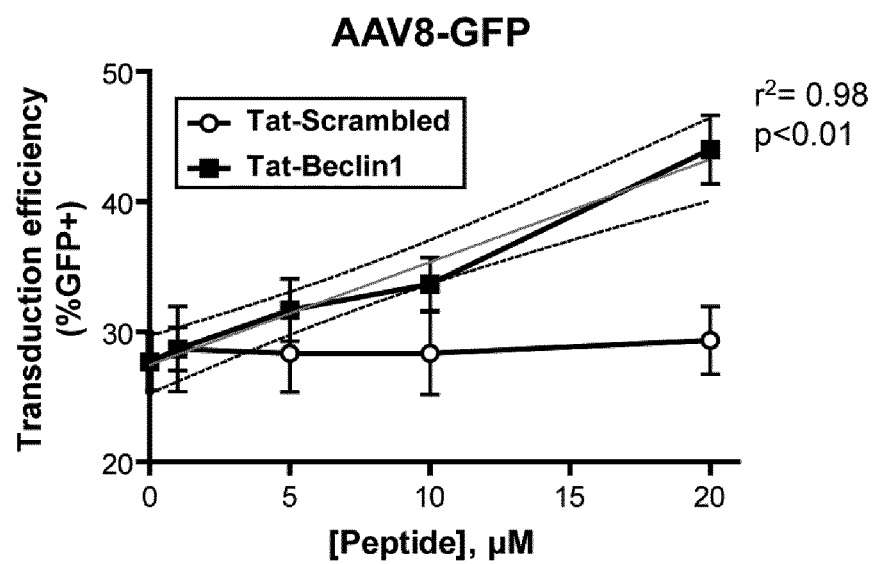

FIG. 6. Tat-Beclin1 enhances cell line transduction with recombinant adeno-associated virus. A) 293T cells were transduced six hours with GFP-expressing recombinant AAV8 (MOI 1000) in absence or presence of the indicated concentrations of Tat-Scrambled or Tat-Beclin1 peptide. After three to 4 days, transduction efficiencies were evaluated by monitoring GFP expression. Data are expressed as the average of three independent experiments performed in duplicate ±SEM and are analyzed using linear regression modeling.

Figure 7:
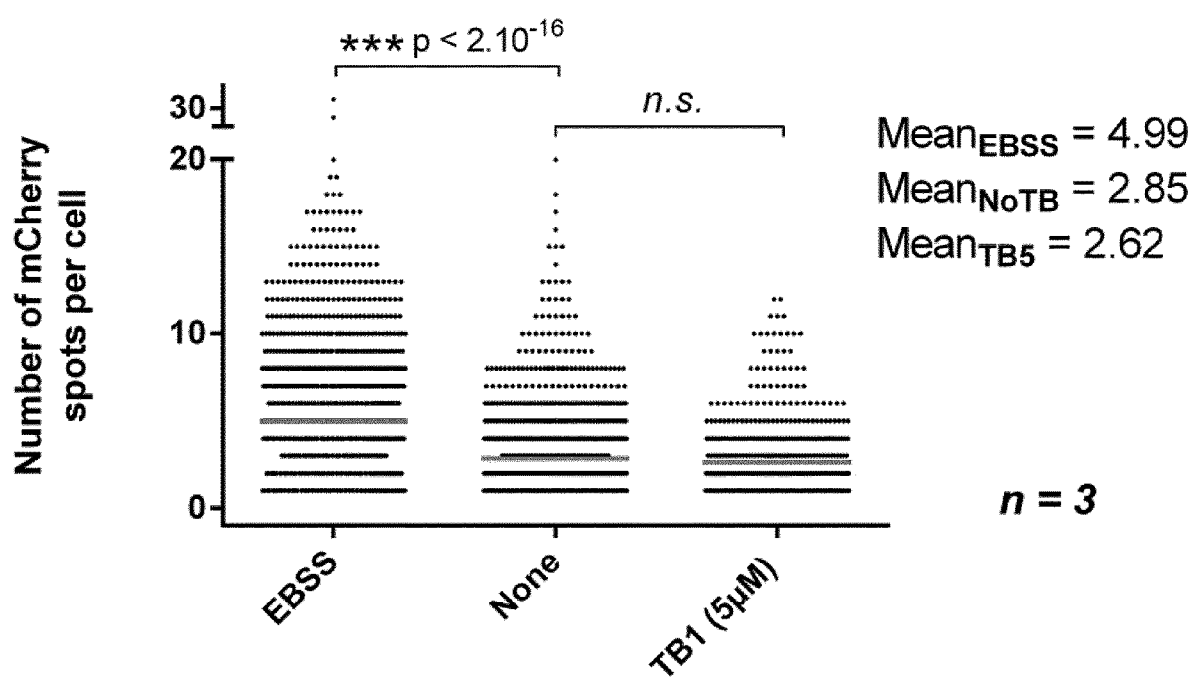

FIG. 7. The optimal dose of Tat-Beclin1 to promote lentiviral transduction is not inducing autophagy. HEK293T cells expressing the mCherry-eGFP-LC3 fusion protein were incubated in the absence or presence of Tat-Beclin1 (5 µM) or in an Earle's Balanced Salt solution (EBSS) for 6 h. Next, cells were analyzed using an imaging flow cytometer. Images of cells were acquired in bright field, in mCherry-fluorescence, and in SSC channel. Data are represented as the number of mCherry spots observed in each individual cell. Bars indicate the mean value of the distributions obtained from three independent experiments. P-values were determined using Mann-Whitney tests. n.s. not statistical.

Figure 8:
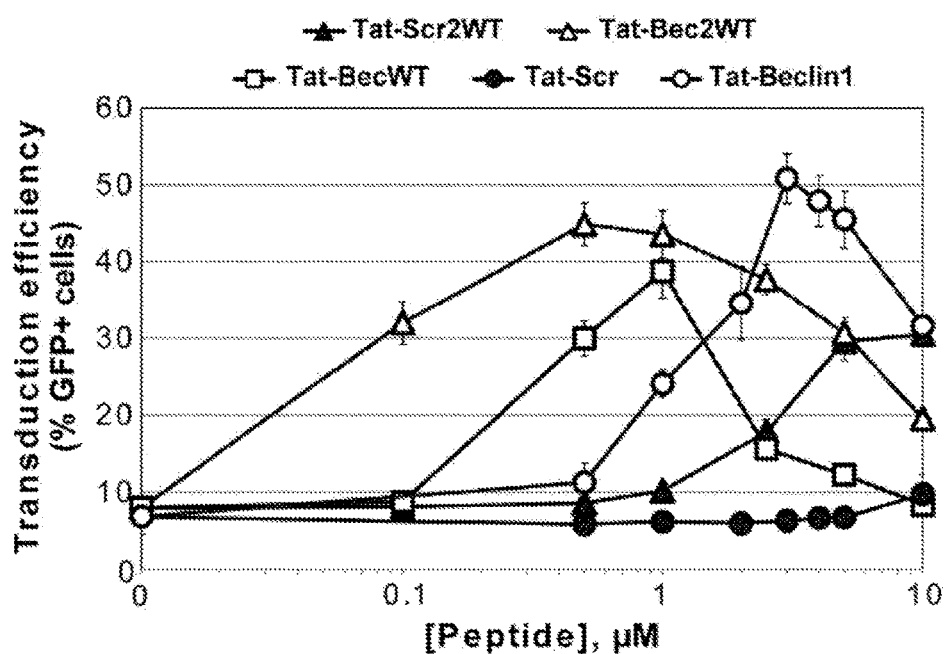

FIG. 8. A Beclin2-derived peptide promotes cell line transduction with VSV-G-LVs at very low doses. A) Primary sequence of Tat-Beclin1, Tat-Beclin1 wild type (Tat-BecWT) and Tat-Beclin2 wild type (Tat-Bec2WT) peptides. B) HCT116 cells were transduced six hours with VSV-G-LVs (2×105 TU/ml) in absence or presence of the indicated concentrations of Tat-Scrambled (Tat-Scr), Tat-Beclin1, Tat-Beclin1 wild type (Tat-BecWT), Tat-Scrambled 2 (Tat-Scr2WT) and Tat-Beclin2 wild type (Tat-Bec2WT) peptides. All the data are expressed as the average of three independent experiments performed in duplicate ±standard error means (SEM).

DETAILED DESCRIPTION

The present invention relates to non-naturally occurring, synthetic peptides comprising, or consisting of:
(i) a CPP moiety; and
(ii) a Beclin-derived peptide moiety.

Both moieties are covalently bound, optionally via an amino acid or non-amino acid linker. In addition, according to the present invention, the peptide may comprise both moieties in any orientation (such as, from the N-terminal to the C-terminal ends: CPP moiety—Beclin-derived moiety; or Beclin-derived moiety—CPP moiety)

Cell-Penetrating Peptide (CPP) Moiety

In the context of the present invention, the term "cell-penetrating peptide" or "CPP" refers to a peptide chain of variable length, without limitation and independently of the mechanism by which the peptide carries out its function, that is known or can be demonstrated to enhance or promote the transfer of a cargo (e.g. a peptide, a nucleic acid, a virus or any other cargo) from an extracellular compartment across a cell membrane such that the cargo is conveyed into a cell where it can effect at least one measurable biological response or function. CPPs may typically have an amino acid composition that either contains a high relative abundance of positively charged amino acids such as lysine or arginine or may have sequences that contain an alternating pattern of polar/charged amino acid and non-polar, hydrophobic amino acids.

Accordingly, in a particular embodiment of the present invention, the CPP moiety consists of an amino acid sequence having from 5 to 50 amino acid residues, in particular from 10 to 20 amino acid residues. In a further particular embodiment, the CPP moiety has an amino acid sequence comprising positively charged residues such as lysine and arginine residues. In another embodiment, the CPP moiety has an amino acid sequence alternating positively charged residues such as lysine or arginine residues, and non-polar, hydrophobic residues such as alanine and leucine residues.

The CPP moiety may be derived from naturally-occurring proteins which are able to translocate across cell membranes such as the *Drosophila* homeobox protein Antennapedia (a transcriptional factor), viral proteins such as the HIV-1 transcriptional factor TAT and the capsid protein VP22 from HSV-1, and/or they may be synthetically-derived, e.g. from chimeric proteins or synthetic polypeptides such as polyarginine. A review on CPPs may be found in Milletti, 2012.

In a particular embodiment, the CPP moiety is a peptide derived from the trans-activator of transcription (tat) peptide of the Human Immunodeficiency Virus (HIV) type-1. In the context of the present invention, a peptide derived from the tat peptide is a tat fragment including an amino acid sequence having cell-penetration properties. In particular, the tat-derived peptide is a peptide comprising, or consisting of, amino acids 47-57 (SEQ ID NO:1), 48-60 (SEQ ID NO:2) or 49-57 (SEQ ID NO:3) of tat.

Other CPPs that may be used, without limitation, in the practice of the present invention include MAP- or antennapedia-derived peptides.

Table 1 lists various representative peptides which may be used.

TABLE 1 list of CPPs

| CPP | Sequence | SEQ ID |
|---|---|---|
| Tat (47-57) | YGRKKRRQRRR | SEQ ID NO: 1 |
| Tat (48-60) | GRKKRRQRRRPPQ | SEQ ID NO: 2 |
| Tat (49-57) | RKKRRQRRR | SEQ ID NO: 3 |
| MAP peptides | KLALKLALKALKAALKA | SEQ ID NO: 4 |
|  | KLALKLALKALKAALKLA | SEQ ID NO: 5 |
| Antennapedia (or penetratin) | RQIKIWFQNRRMKWKK | SEQ ID NO: 6 |

TABLE 1-continued list of CPPs

| CPP | Sequence | SEQ ID |
|---|---|---|
| Penetratin derivatives | RRMKWKK | SEQ ID NO: 7 |
| | NRRMKWKK | SEQ ID NO: 8 |
| | QNRRMKWKK | SEQ ID NO: 9 |
| | FQNRRMKWKK | SEQ ID NO: 10 |
| | RREKWKK | SEQ ID NO: 11 |
| | RRQKWKK | SEQ ID NO: 12 |
| | KRMKWKK | SEQ ID NO: 13 |
| | RKMKWKK | SEQ ID NO: 14 |
| | RROKWKK | SEQ ID NO: 15 |
| | RRMKQKK | SEQ ID NO: 16 |
| | RRMKWFK | SEQ ID NO: 17 |
| | RORKWKK | SEQ ID NO: 18 |
| | RRMWKKK | SEQ ID NO: 19 |
| | RRMKKWK | SEQ ID NO: 20 |
| | Wherein "O" denotes ornithine | |
| D-penetratin | rqikiwfqnrrmkwkk | SEQ ID NO: 21 |
| Pegelin (SynB) | RGGRLSYSRRRFSTSTGR | SEQ ID NO: 22 |
| VP22 | DAATATRGRSAASRPTERPRAPARSASRPRRVD | SEQ ID NO: 23 |
| Transportan | GWTLNSAGYLLGKINLKALAALAKKIL | SEQ ID NO: 24 |
| Transportan-10 | AGYLLGKINLKALAALAKKIL | SEQ ID NO: 25 |
| KALA | WEAKLAKALAKALAKHLAKALAKALKACEA | SEQ ID NO: 26 |
| Pep-1 | KETWVVETWVVTEWSQPKKKRKV | SEQ ID NO: 27 |
| Pep-2 | KETWFETWFTEWSQPKKKRKV | SEQ ID NO: 28 |
| MPG | GALFLGFLGAAGSTMGAWSQPKSKRKV | SEQ ID NO: 29 |
| Vectocell peptides | VKRGLKLRHVRPRVTRMDV | SEQ ID NO: 30 |
| | SRRARRSPRHLGSG | SEQ ID NO: 31 |
| | LRRERQSRLRRERQSR | SEQ ID NO: 32 |
| | GAYDLRRRERQSRLRRRERQSR | SEQ ID NO: 33 |
| Wr-T transporter | KETWVVETWVVTEWVVTEWSQGPGrrrrrrrrr | SEQ ID NO: 34 |
| | "r" = D enantiomer arginine | |
| R7 | RRRRRRR | SEQ ID NO: 35 |
| LAH4 and | KKALLALALHHLAHLALHLALALKKA | SEQ ID NO: 36 |
| LAH4 derivatives | KKALLAHALHLLALLLAHLAHALKKA | SEQ ID NO: 37 |
| | KKALLAHALHLLALLALHLAHALA | SEQ ID NO: 38 |
| | RRALLAHALHLLALLALHLAHALRRA | SEQ ID NO: 39 |
| | KKALLAHALAHLLALLALHLAHLKKA | SEQ ID NO: 40 |
| | KKALLALALHHLALLALHLAHALKKA | SEQ ID NO: 41 |
| | KKALLALALHHLALLAHHLALALKKA | SEQ ID NO: 42 |
| | KKALLHLALLHAALLAHHLALALKKA | SEQ ID NO: 43 |
| | KKALLHLALLHAALLALAHLAAHLKKA | SEQ ID NO: 44 |
| | KKALLHLALLLAALHAHLAALHLKKA | SEQ ID NO: 45 |
| | KKALLAHALHLLAALALHLAHLLKKA | SEQ ID NO: 46 |
| | KKALLLAALHHLAALALHLAHLLKKA | SEQ ID NO: 47 |
| | KKALLLAALHHLLALAHHLAALLKKA | SEQ ID NO: 48 |
| | KKALLHAALAHLLALAHHLLALLKKA | SEQ ID NO: 49 |
| | KKALLHALLAHLAALLHALLAHLKKA | SEQ ID NO: 50 |
| | KKALLHALLAALLAHLHALLAHLKKA | SEQ ID NO: 51 |
| | KALLHAALAHLLALAHHLLALLKKA | SEQ ID NO: 52 |
| | KKKLLHAALAHLLALAHHLLALLKKA | SEQ ID NO: 53 |
| | KKALLHAALAHLLALAHHLLALLA | SEQ ID NO: 54 |
| | KKALLHAALAHLLALAHHLLALLKK | SEQ ID NO: 55 |
| | KKLLHAALAHLLALAHHLLALLKK | SEQ ID NO: 56 |
| | KKALLHAALAHLLALAHHLLALKK | SEQ ID NO: 57 |
| | KKLHAALAHLLALAHHLLALLKK | SEQ ID NO: 58 |
| | KKLHAALAHLLALAHHLLAKK | SEQ ID NO: 59 |
| | KKALLHAALAHLLALAAALLALLKKA | SEQ ID NO: 60 |
| | KKALLAAALAALLALAAALLALLKKA | SEQ ID NO: 61 |
| | KKLLLHALLAHLLALLHHLLALLKKL | SEQ ID NO: 62 |

In a particular embodiment, the CPP moiety comprises, or consists of, a peptide sequence selected from any of SEQ ID NO:1-62, or a variant thereof having at least 50%, at least 60%, at least 70%, at least 80%, at least 85%, at least 90% or at least 95% sequence identity to any of SEQ ID NO:1-62 and retaining at least a part of its capacity to enhance the delivery of a cargo molecule into a cell.

In a particular embodiment, the CPP moiety is selected from the group consisting of SEQ ID NO:1 to SEQ ID NO:4, in particular from SEQ ID NO:1 and SEQ ID NO:4.

Beclin Peptide Moiety

In the context of the present invention, the Beclin-derived peptide moiety corresponds to an amino acid sequence derived from a Beclin protein.

In the context of the present invention, a "functional variant" or a "derivative" of a Beclin peptide is a peptide capable of improving transduction efficiency of a virus, when said functional variant or said derivative is fused to a CPP moiety. In particular, the functional variant is capable, when fused to a CPP moiety, of improving transduction efficiency of a virus by at least 10%, at least 20%, or at least 30% or more, preferably by at least 30%. More particularly, the functional variant is capable, when fused to a CPP moiety, of improving transduction efficiency of a HIV-1 derived lentiviral vector (LV) pseudotyped with envelope glycoproteins (GPs) from the vesicular stomatitis virus (VSV-G) by at least 10%, at least 20%, or at least 30% or more, preferably at least 30%. Even more particularly, the functional variant is capable, when fused to a CPP moiety, of improving transduction efficiency of hCD34+ cells by a HIV-1 derived lentiviral vector (LV) pseudotyped with envelope glycoproteins (GPs) from the vesicular stomatitis virus (VSV-G) by at least 10%, at least 20%, at least 30% or more. In a further particular embodiment, a functional variant of a Beclin peptide further has at least 50%, at least 60%, at least 70%, at least 75%, at least 80% and most particularly at least 83% sequence identity to the sequence of the parent Beclin peptide (i.e., from the peptide it derives from), such as from the Beclin peptide shown in SEQ ID NO:65 or 89. In a particular embodiment, the sequence of the Beclin-derived peptide moiety includes an amino acid sequence wherein addition, deletion or substitution of 1 to 6 amino acid residues has been made into the parent Beclin peptide, such as into the sequence shown in SEQ ID NO:65 or 89. In a particular aspect, the Beclin-derived peptide moiety is a Beclin-1 or Beclin-2 peptide moiety comprising 1, 2, 3, 4, 5 or 6 amino acid substitutions, such as 4, 5 or 6 amino acid substitutions in SEQ ID NO:65 or 89.

According to a particular embodiment, the Beclin-derived moiety length is comprised between 14 to 22 amino acid residues, such as from 16 to 20 amino acid residues in length, in particular a peptide consisting of 16, 17, 18, 19 or 20 amino acid residues in length. In a particular embodiment, the Beclin-derived moiety length is of 18 amino acid residues.

In a particular aspect, the Beclin-derived peptide moiety comprises or consists of the sequence of general formula (I):

$$N_1\ N_2\ N_3\ N_4\ N_5\ N_6\ T\ F\ N_9\ I\ N_{11}\ N_{12}\ N_{13}\ G\ N_{15}\ N_{16}\ N_{17}\ N_{18} \quad (I)$$

wherein:

$N_1$ is a polar amino acid or is I, in particular T or I, and more particularly I;

$N_2$ is a polar amino acid, in particular N, D or S, and more particularly N;

$N_3$ is a hydrophobic amino acid or C, in particular V, C or I, and more particularly C;

$N_4$ is a hydrophobic amino acid, in particular F or L, and more particularly F;

$N_5$ is a polar amino acid, in particular N, T, S, R or Q, and more particularly T;

$N_6$ is a hydrophobic amino acid, in particular A or V, and more particularly A;

$N_9$ is a polar amino acid, in particular H, E or T, and more particularly E;

$N_{11}$ is W, S, G or R, in particular W;

$N_{12}$ is a polar amino acid or is V, in particular H, V, D, Q or E, and more particularly V;

$N_{13}$ is a polar amino acid or is A, in particular S, E, D, A, and more particularly E;

$N_{15}$ is Q, P, S or E, in particular P;

$N_{16}$ is a hydrophobic amino acid, in particular F, L, V or I, and more particularly L;

$N_{17}$ is a hydrophobic amino acid, in particular G, A or P, and more particularly G;

$N_{18}$ is T, V or I, in particular V.

In another particular aspect, the Beclin-derived peptide moiety comprises or consists of the sequence of general formula (II):

$$N_1\ N_2\ N_3\ F\ N_5\ N_6\ T\ F\ N_9\ I\ N_{11}\ N_{12}\ N_{13}\ G\ N_{15}\ N_{16}\ N_{17}\ N_{18} \quad (II)$$

wherein:

$N_1$ is a polar amino acid or is I, in particular T or I, and more particularly I;

$N_2$ is a polar amino acid, in particular N, D or S, and more particularly N;

$N_3$ is a hydrophobic amino acid, in particular V, C or I, and more particularly C;

$N_5$ is a polar amino acid, in particular N, T, S, R or Q, and more particularly T;

$N_6$ is a hydrophobic amino acid, in particular A or V, and more particularly A;

$N_9$ is a polar amino acid, in particular E or T, and more particularly E;

$N_{11}$ is W, S, G or R, in particular W;

$N_{12}$ is a polar amino acid or is V, in particular H, V, D, Q or E, and more particularly V;

$N_{13}$ is a polar amino acid or is A, in particular S, E, D, A, and more particularly E;

$N_{15}$ is P or S, in particular P;

$N_{16}$ is a hydrophobic amino acid, preferably L, V or I, and more particularly L;

$N_{17}$ is a hydrophobic amino acid, preferably G, A or P, and more particularly G;

$N_{18}$ is a hydrophobic amino acid, in particular V or I, and more particularly V.

The term "polar amino acid" refers to amino acids comprising hydrophilic side-chains that prefer to reside in an aqueous (i.e. water) environment. These side chains can thus be involved in hydrogen bonding interactions. The term "polar amino acid" comprises "polar charged amino acids" such as D, E, K, R, H and "polar uncharged amino acids" such as S, T, Y, C, N, and Q.

The term "hydrophobic amino acid" refers to amino acids comprising non-polar side chains that are uncharged at physiological pH. Hydrophobic side chains are chemically unreactive and tend to aggregate rather than be exposed to the aqueous environment. The term "hydrophobic amino acid" comprises G, A, L, I, V, P, F, W, and M.

As used herein, "amino acids" are sometimes specified using the standard one letter code: Alanine (A), Serine (S), Threonine (T), Aspartic acid (D), Glutamic acid (E) Asparagine (N), Glutamine (Q), Arginine (R), Lysine (K), Isoleucine (I), Leucine (L), Methionine (M), Valine (V), Phenylalanine (F), Tyrosine (Y), Tryptophan (W), Proline (P), Glycine (G), Histidine (H), Cysteine (C). Synthetic and non-naturally occurring amino acid analogues (and/or peptide linkages) are included.

In a particular embodiment, the Beclin-derived moiety is derived from a human Beclin protein, such as the human Beclin-1 protein shown in SEQ ID NO:63 or the human Beclin-2 protein shown in SEQ ID NO:64:

SEQ ID NO: 63:
MEGSKTSNNSTMQVSFVCQRCSQPLKLDTSFKILDRVTIQELTAPLLTTA

-continued
QAKPGETQEEETNSGEEPFIETPRQDGVSRRFIPPARMMSTESANSFTLI

GEASDGGTMENLSRRLKVTGDLFDIMSGQTDVDHPLCEECTDTLLDQLDT

QLNVTENECQNYKRCLEILEQMNEDDSEQLQMELKELALEEERLIQELED

VEKNRKIVAENLEKVQAEAERLDQEEAQYQREYSEFKRQQLELDDELKSV

ENQMRYAQTQLDKLKK<u>TNVFNATFHIWHSGQFGT</u>INNFRLGRLPSVPVEW

NEINAAWGQTVLLLHALANKMGLKFQRYRLVPYGNHSYLESLTDKSKELP

LYCSGGLRFFWDNKFDHAMVAFLDCVQQFKEEVEKGETRFCLPYRMDVEK

GKIEDTGGSGGSYSIKTQFNSEEQWTKALKFMLTNLKWGLAWVSSQFYNK

SEQ ID NO: 64:
MSSIRFLCQRCHQALKLSGSSESRSLPAAPAPTSGQAEPGDTREPGVTTR

EVTDAEEQQDGASSRSPPGDGSVSKGHANIFTLLGELGAMHMLSSIQKAA

GDIFDIVSGQAVVDHPLCEECTDSLLEQLDIQLALTEADSQNYQRCLETG

ELATSEDEAAALRAELRDLELEEARLVQELEDVDRNNARAAADLQAAQAE

AAELDQQERQHYRDYSALKRQQLELLDQLGNVENQLQYARVQRDRLKEI<u>N</u>

<u>CFTATFEIWVEGPLGV</u>INNFRLGRLPTVRVGWNEINTAWGQAALLLLTLA

NTIGLQFQRYRLIPCGNHSYLKSLTDDRTELPLFCYGGQDVFLNNKYDRA

MVAFLDCMQQFKEEAEKGELGLSLPYGIQVETGLMEDVGGRGECYSIRTH

LNTQELWTKALKFMLINFKWSLIWVASRYQK

In a particular embodiment, the Beclin-2-derived peptide moiety includes the amino acids 249 to 266 in SEQ ID NO:64 (underlined sequence: INCFTATFEIWVEGPLGV referred as SEQ ID NO:89). In a particular embodiment, the Beclin-2-derived peptide moiety comprises, or consists of, the sequence shown in SEQ ID NO:89, or comprises, or consists of, a sequence corresponding to a functional variant thereof as defined above. In a particular embodiment, the functional variant of the Beclin-2-derived peptide has phenylalanine residues at its positions corresponding to amino acids 252 and 256 of SEQ ID NO:64.

In a particular embodiment, the Beclin-2-derived peptide moiety or the functional variant thereof is derived from Beclin-2 of any species, including without limitations human, mouse, rabbit, pig, horse, panda or cow Beclin-2. The following Table 2 corresponds to the alignment of amino acids from 249 to 266 of human Beclin-2 sequence and corresponding sequences in mouse, rabbit, pig, horse, panda and cow.

TABLE 2

| Alignment of Beclin-2 sequences | | |
|---|---|---|
| Human Beclin-2 (249-266) | INCFTATFEIWVEGPLGV | SEQ ID NO: 89 |
| Mouse Beclin-2 (262-279) | TNIFNATFTISDEGPLGV | SEQ ID NO: 92 |
| Horse Beclin-2 (253-270) | INVFSVTFEIGHSGPVGV | SEQ ID NO: 93 |
| Panda Beclin-2 (645-662) | TNVFNATFEIRHDGPVGI | SEQ ID NO: 94 |
| Pig Beclin-2 (244-261) | TNVFRATFEIRHAGPIAI | SEQ ID NO: 95 |
| Cow Beclin-2 (248-265) | TDVFNATFEIVVQDGPLPV | SEQ ID NO: 96 |
| Rabbit Beclin-2 (238-255) | TSIFQVTFEIREEGSVGI | SEQ ID NO: 97 |

In a particular embodiment, the Beclin-derived peptide derives from a Beclin-2 peptide selected in the group consisting of the sequences of Table 2.

In a particular embodiment, the Beclin-1-derived peptide moiety includes the β1 sheet of Beclin-1, or a functional variant of the β1 sheet of Beclin-1, which is located from amino acids 274 to 279 in SEQ ID NO:63. In a further particular embodiment, the Beclin-1 derived peptide moiety includes the L1 loop and the β1 sheet of Beclin-1. In another embodiment, the Beclin-1 derived peptide moiety includes at least a C-terminal part or all of amino acids 250-262 of SEQ ID NO:63 (corresponding to the al helix of Beclin-1), the L1 loop and the β1 sheet of Beclin-1. The sequence which is underlined in SEQ ID NO:63 is referred to as SEQ ID NO:65 in the following description (SEQ ID NO:65: TNVFNATFHIWHSGQFGT). It corresponds to a fragment of the evolutionary conserved domain ($ECD_{267-284}$) of Beclin-1. In a particular embodiment, the Beclin-1-derived peptide moiety comprises, or consists of, the sequence shown in SEQ ID NO:65, or comprises, or consists of, a sequence corresponding to a functional variant thereof as defined above. In a particular embodiment, the functional variant of the Beclin-1-derived peptide has phenylalanine residues at its positions corresponding to amino acids 270 and 274 of SEQ ID NO:63.

The Beclin-1-derived peptide shown in SEQ ID NO:66, which corresponds to SEQ ID NO:65 with substitutions at positions 9, 13 and 15 of SEQ ID NO:65 (corresponding to positions 275, 279 and 281 of SEQ ID NO:63) and phenylalanine residues maintained at the amino acid positions corresponding to positions 270 and 274 of SEQ ID NO:65, is an illustrative functional variant according to the present invention:

```
                                    SEQ ID NO: 66
TNVFNATFEIWHDGEFGT
```

In a particular aspect, the Beclin-1-derived peptide moiety may comprise from 10 to 60 amino acids, in particular from 15 to 55, in particular 18 to 50, in particular 18 to 49 amino acids (such as 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 and 49 amino acids), in particular from 18 to 35 amino acids, more particularly from 18 to 33 amino acids (such as 18, 19, 20, 21, 22, 23, 24, 25, 26, 27, 28, 29, 30, 31, 32 and 33 amino acids).

In a particular embodiment, the Beclin-1-derived peptide moiety comprises amino acids 270-282, in particular amino acids 267-284 of SEQ ID NO:63 (i.e. SEQ ID NO:65), or a variant thereof as described above, and at least one or more amino acids of the Beclin-1 protein contiguous to amino acids 267-284 on either ends, or both. For example, the Beclin-1-derived peptide moiety may in particular further comprise 1, 2, 3, 4, 5, 6, 7, 8, 9, 10, 11, 12, 13, 14, 15, 16 or 17 amino acids contiguous to amino acids 267-284 in SEQ ID NO:63, in addition to the sequence shown in SEQ ID NO:65. For example, the Beclin-1-derived moiety may further include amino acids 250-266 or 256-266. It may also include, either alternatively or in addition to the amino acids mentioned in the preceding sentence, amino acids 285-296 or 285-298 of SEQ ID NO:63, in addition to the sequence of SEQ ID NO:65 or to a functional variant thereof such as SEQ ID NO:66. Furthermore, the present invention also envisions functional variants of SEQ ID NO:65 that include a part of said sequence shown in SEQ ID NO:65, such as a functional variant including amino acids 268-284, 269-284, 270-284, 267-283 or 267-282 of SEQ ID NO:63. Additionally, the functional variant may be a variant of the sequence shown in SEQ ID NO:66, wherein 1, 2 or 3 amino acids are deleted from either their N-terminal or C-terminal end, or from both ends.

Illustrative functional variants of the Beclin-1 peptide according to the invention include:

| | |
|---|---|
| FNATFEIWHDGEFGT | SEQ ID NO: 67 |
| TNVFNATFEIVVHDGEF | SEQ ID NO: 68 |
| YAQTQLDKLKKTNVFNATFEIWHDGEFGT | SEQ ID NO: 69 |
| TNVFNATFEIVVHDGEFGTINNFRLGRLPSV | SEQ ID NO: 70 |
| VENQMRYAQTQLDKLKKTNVFNATFEIVVHDGEF | SEQ ID NO: 71 |
| FNATFEIWHDGEFGTINNFRLGRLPSVPV | SEQ ID NO: 72 |
| FEIVVHDGEFGTINNFRLGRLPSVPV | SEQ ID NO: 73 |

Fusion Peptide

As mentioned above, the peptide of the invention comprises a CPP moiety and a Beclin-derived moiety covalently linked together and is therefore a fusion peptide.

Linkage of the two parts of the peptide may be done directly by a covalent bond, or via a linker moiety.

The peptide of SEQ ID NO:74 is an example of a direct linkage of the two peptide moieties, wherein the CPP moiety is the Tat sequence shown in SEQ ID NO:1, and the Beclin-derived peptide moiety consists of the amino acid sequence shown in SEQ ID NO:66 fused to amino acids 285-296 of SEQ ID NO:63:

```
                                    SEQ ID NO: 74
YGRKKRRQRRR TNVFNATFEIWHDGEFGTINNFRLGRLPSV
```

The peptide of SEQ ID NO:90 is an example of a direct linkage of the two peptide moieties, wherein the CPP moiety is the Tat sequence shown in SEQ ID NO:1, and the Beclin-derived peptide moiety consists of the amino acid sequence shown in SEQ ID NO:89:

```
                                    SEQ ID NO: 90
YGRKKRRQRRR INCFTATFEIWVEGPLGV
```

In a particular embodiment, the peptide comprises a linker. The linker may be a peptide comprising from 1 to 25 amino acids, in particular from 1 to 5 amino acids. In a particular embodiment, the linker is a single neutral (i.e. neutral at physiological pH) amino acid such as a G, A, V, S, Y or T, in particular G. Alternatively, the linker may be a dipeptide of neutral amino acids such as a dipeptide selected from GG, AA, GA, AG, AS, AY, GS, GT, GV, AV, SV, TV, VG, VA and VT.

In another particular embodiment, the linker is a non-peptidic linker such as a —(CH$_2$)$_n$— linker, wherein n is an integer comprised between 1 and 6.

From the N-terminal end to the C-terminal end, the peptide of the invention may comprise, in this order:
a CPP moiety and a Beclin-derived moiety, optionally linked via a linker as described above; or
a Beclin-derived moiety and a CPP moiety, optionally linked via a linker as described above.

In a particular embodiment, the peptide of the invention comprises, from its N-terminal end to its C-terminal end, a CPP moiety and a Beclin-derived moiety, optionally linked via a linker as described above. In a further particular embodiment, the peptide of the invention comprises, in this order, a CPP moiety, a linker (in particular a dipeptide linker such as a GG dipeptide) and a Beclin-derived moiety.

In another particular embodiment, the peptide of the invention comprises, from its N-terminal end to its C-terminal end, a Beclin-derived moiety and a CPP moiety, optionally linked via a linker as described above. In a further particular embodiment, the peptide of the invention comprises, in this order, a Beclin-derived moiety, a linker (in particular a dipeptide linker such as a GG dipeptide) and a CPP moiety.

In a particular embodiment, the peptide of the invention is a fusion peptide comprising, in this order, (i) a CPP moiety which is a Tat sequence (e.g. one of the sequences shown in SEQ ID NO:1, 2 and 3, and in particular the sequence shown in SEQ ID NO:1) or a MAP sequence (e.g. SEQ ID NO:4 or 5), (ii) a dipeptide linker such as the GG dipeptide, and (iii) a Beclin-derived moiety of formula (I) or (II), such as a Beclin-1-derived moiety such as one of SEQ ID NO:65-73 or a Beclin-2-derived moiety such as SEQ ID NO:89. In particular, the peptide implemented in the invention is the peptide shown in SEQ ID NO: 75: YGRKKRRQRRR GG TNVFNATFEIWHDGEFGT; SEQ ID NO: 76: KLALKLA-LKALKAALKA G TNVFNATFEIWHDGEFGT; SEQ ID NO: 77: YGRKKRRQRRR GG TNVFNATFHIWHSGQFGT; SEQ ID NO: 78: YGRKKRRQRRR GG YAQTQLDKLKKTNVFNAT-FEIWHDGEFGT; SEQ ID NO: 79: YGRKKRRQRRR GG TNVFNATFEIWHDGEFGTINNFRLGRLPSV; SEQ ID NO: 80: YGRKKRRQRRR GG TNVFNATFHIWHSGQFGTINNFRLGRLPSV; SEQ ID NO: 81: YGRKKRRQRRR GG VENQM- RYAQTQLDKLKKTNVFNATFEIWHDGEF; SEQ ID NO: 82: YGRKKRRQRRR GG FEIWHDGEFGTINNFRL-GRLPSVPV; SEQ ID NO: 83: YGRKKRRQRRR GG FNATFEIWHDGEFGTINNFRLGRLPSVPV; or SEQ ID NO:91: YGRKKRRQRRR GG INCFTATFEIWVEGPLGV.

According to a particular embodiment, the invention also encompasses retro, inverso or retro-inverso derivatives of the peptides defined above, which retain the transduction promoting properties herein disclosed. In a particular embodiment, the invention relates to a retro-inverso derivative of the peptides as defined above. In particular, retro-inverso derivatives of the peptides of the invention are suitable for in vivo uses since they are more resistant to proteolytic degradation. The peptides may comprise at least one D amino acid as well as iminoamino acids and rare amino acids. The invention also relates to peptide mimetics of the peptides according to the invention. These can be characterized for example by a modification of one or more peptide bonds, for example, by a reverse peptide bond or by an ester bond. The invention also includes derivatives of the peptides described above, comprising amino acids different than alpha-amino acids, such as beta or gamma-amino acids.

Uses of the Fusion Peptide

The peptides of the invention promote viral infection of a cell. As used herein, "viruses" relates to natural occurring viruses as well as artificial viruses. For example, paramyxovirus (such as respiratory syncytial virus, measle virus), orthomyxovirus (such as influenza virus), flavivirus (such as hepatitis C virus), hepadnavirus (such as hepatitis B virus), rhabdovirus (such as rabies, VSV), coronavirus (such as SARS), togavirus (such as Sindbis virus, Chikungunya virus), filovirus (such as ebola virus), arenavirus, poxvirus, herpesvirus, bunyavirus, bornavirus, arterivirus, baculovirus, parvovirus such as adeno-associated virus. According to a particular embodiment, the viruses are artificial viruses, which may for instance comprise a cargo, such as a cargo useful for a therapeutic, diagnostic or any other purpose (e.g. useful for conducting functional studies within a target cell). Illustrative cargos include nucleic acid cargos such as a DNA or RNA sequence encoding a product, in particular a gene therapy product (for example a protein or RNA, such as an antisense RNA or a shRNA) or a diagnostic product. Furthermore, according to the present invention, the virus may be a virus-like particle (or VLP) which may further contain a cargo such as a protein cargo, a nucleic acid cargo (such as a DNA or RNA cargo), a diagnostic cargo or a drug cargo. In the context of the present invention, a virus is either an enveloped or non-enveloped virus. Parvoviruses such as adeno-associated viruses (or AAVs) are illustrative non-enveloped viruses. In a preferred embodiment, the viruses are enveloped viruses. In preferred embodiments, the viruses are retroviruses and in particular lentiviruses. The inventors have shown that peptides of the present invention can promote the infection of eukaryotic cells with HIV-1 derived lentiviral vectors (LVs) pseudotyped with envelope glycoproteins (GPs) from the vesicular stomatitis virus (VSV-G), the modified feline endogenous retrovirus (RD114TR), and the modified gibbon ape leukemia virus (GALVTR). The inventors have even shown that the peptides of the invention efficiently promote entry of other viruses such as parvoviruses, including adeno-associated viruses, thereby demonstrating their broad efficiency. In view of the efficiency of the transduction obtained with the peptides of the invention and the diversity of the viral vectors and GPs used in the disclosed experiments, it is clear that the present peptides can be used as a general means for increasing transduction efficiencies of enveloped and non-enveloped viruses in eukaryotic cells. Therefore, it is also expected that the peptides of the invention may promote infection of eukaryotic cells with a number of other viruses or other pseudotyped viruses, such as lentiviruses pseudotyped with various envelope glycoproteins (Levy, 2015), for instance the amphotrophic murine leukemia virus GP (A-MLV) or the modified baboon endogenous virus GP (BaEVTR) or with non-enveloped viruses such as parvoviruses, in particular AAVs such as a recombinant AAV vector.

The target cells can be any kind of eukaryotic cells such as mammalian cells, in particular human, mouse, rat, monkey, dog or hamster cells. In a particular embodiment, the target cell is a CD34+ cell, in particular a CD34+ cell collected from a patient in need of a gene therapy of his/her hematopoietic lineage. Other representative, non-limiting, target tissues/cells are skin, muscle, liver, eye, neurons, lymphocytes, fibroblasts, keratinocytes, adipocytes, myoblasts, hepatocytes, tumor cells and more generally any eukaryotic cell that is known or will be identified as a target of a virus. The inventors show in the experimental part below that transduction of a wide variety of cells may be obtained thanks to the peptides of the invention, thereby demonstrating their broad efficiency and applicability.

In methods disclosed herein, the peptide of the invention is used in an effective amount. The term "effective amount" of the peptide herein denotes the amount required for increasing significantly the transduction efficiency of a viral vector. This effective amount will generally depend on the particular peptide tested, the target cell and the viral vector implemented. In particular, the effective amount is an amount of the peptide inducing an increase in the efficiency of transduction of a viral vector without inducing or increasing the autophagy process. This amount can be determined according to methods well known in the art, in particular according to the above method implementing a reporter assay and illustrated in the examples. For example, the inventors have surprisingly shown of the previously disclosed Tat-Beclin1 peptide (Shoji-Kawata et al., 2013) optimally promotes virus transduction of HCT116 cells or CD34+ cells with VSV-G-LV or GALVTR-LV at a concentration which is low, typically at a concentration comprised between 1 and 20 µM, such as 2.5 and 20 µM, depending on the cell type which is transduced. Moreover, the present inventors have shown that the Tat-Beclin-2 peptide is a potent enhancer of lentiviral transduction at even lower doses comprised between 0.01 µM to about 10 µM, in particular between 0.1 and 5 µM. Typical concentration ranges for using the peptides of the invention include a concentration of between 0.01 µM and 20 µM, such as between 1 and 20 µM, such as 2.5 and 20 µM, in particular between 3 and 15 µM, more particularly between 4 and 12 µM, such as a concentration of 4, 5, 6, 7, 8, 9 or 10 µM. In a particular embodiment, the peptide of the invention is used at a concentration of about 5 µM or about 10 µM.

In a particular embodiment, the peptide of the invention, in particular a Tat-Beclin-1 peptide, is used in an effective amount comprised between 0.01 µM and 5 µM, in particular between 1 µM and 5 µM.

According to a further aspect, the invention relates to a complex of a peptide of the invention with a virus particle, in particular non-enveloped (such as a parvovirus, for example an AAV vector) or an enveloped virus particle, more particularly with an enveloped viral vector for gene therapy. Moreover, another aspect of the invention relates to a method for preparing such a complex, which comprises mixing the peptide with a viral particle.

According to another aspect, the invention relates to a mixture of a peptide of the invention with a virus particle (in particular an enveloped virus particle or non-enveloped virus particle, more particularly with an enveloped viral vector for gene therapy) and with a cell. Moreover, another aspect of the invention relates to a method for preparing such mixture, which comprises mixing the peptide, with the viral particle and the cell.

The peptides according to the invention can be used in pharmaceutical compositions. Thus, the present invention relates to a composition comprising a peptide as defined above and a suitable pharmaceutically acceptable vehicle. The pharmaceutical compositions of the invention contain one or more of the peptides according to the invention, or a physiologically acceptable salt of the peptide(s). Pharmaceutical compositions according to the invention can also contain pharmaceutically usual auxiliary agents which contribute, for example, to the solubility, stability or sterility of the composition or increase the efficiency of uptake into the body.

An aspect of the invention also relates to a peptide as defined above, for use as a medicament. In a particular embodiment, the medicament is used for increasing the efficiency of a gene therapy viral vector (D'Costa et al., 2009).

The form and content of the pharmaceutical composition which contains the peptide(s) depends on the route of administration. Preferably, galenic formulations and application forms are selected in which the peptide(s) arrive(s) at the target site in a non-degraded condition. The medicament can be administered locally as injection, drops, spray, tablets, suppositories, cream, ointments, gel etc. It is possible to perform the administration as a bolus or repeatedly over a period of time.

The peptide, complex or pharmaceutical composition or medicament of the invention can be administered in vivo via a local or systemic route, for example by injecting it via the intramuscular, intravenous, intra-arterial, intra-peritoneal or intracranial route. The invention thus also relates to a method for gene therapy, comprising administering to a patient in need thereof a peptide, complex or pharmaceutical composition as described above. The method comprises also administering a virus vector for gene therapy before, after or together with the administration of the peptide of the invention. The virus or viral vector for use in gene therapy according to the present invention includes a therapeutic gene, as is well understood in the art.

According to one aspect, the peptide, complex or pharmaceutical composition or medicament is used in an ex vivo method for cell therapy. In this aspect, the peptide, complex, pharmaceutical composition or medicament is used for enhancing gene therapy viral vector entry into a cell collected from a patient, wherein said cell is intended to be genetically modified thanks to the gene therapy viral vector. In a particular embodiment, the cell is a hematopoietic stem/progenitor cell, such as a hCD34+ cell. The cell may be mixed with a peptide of the present invention and gene therapy viral vector in order to correct any defect detected in said cell. In particular, this ex vivo method is useful for intravenous injection in patients of genetically modified-hCD34+ cells following transduction with a mix of peptide and viral vectors such as HIV-1 derived lentiviral vectors, expressing a gene of interest encoding a product (for example a protein or a therapeutic RNA) useful for the treatment of a disease. For example, the therapeutic product may be the Wiskott-Aldrich Syndrome protein to correct the Wiskott Aldrich syndrome, the IL2 receptor gamma chain to correct the Severe Combined Immune Deficiency 1, the gp91phox protein to correct the Chronic Granulomatous Disease, the adenosine deaminase (ADA) to correct adenosine deaminase deficiency (or ADA-SCID), the β-globin to correct thalassemias, the β-globin or the γ-globin to correct sickle cell disease, the Fanconi anemia protein (such as FA-A) to correct Fanconi anemia, the ATP-binding cassette protein to correct childhood cerebral adreno-leukodystrophy or the Arylsulfatase A to correct metachromatic leukodystrophy. Present invention may also be used for other ex vivo gene therapies, such as therapies based on chimeric antigen receptor (CAR)-T cell. In a particular aspect, the invention also relates to a composition comprising a peptide as described above in a culture medium, said composition being intended for use as an infection promoting reagent for facilitating the transduction of a cell with a virus or viral vector, in particular a non-enveloped or enveloped virus or viral vector. Thus, the invention also relates to a virus infection promoting reagent comprising a peptide according to the present invention, in a suitable medium, in particular in a suitable culture medium.

According to another aspect, the invention also relates to an isolated polynucleotide encoding the peptide of the invention. The polynucleotide of the invention may comprise different nucleotide chemistries, such as DNA, RNA or chemically modified nucleotides.

In another aspect, the invention relates to a nucleic acid construct comprising the polynucleotide operationally linked to at least one control sequence that directs the production for the peptide in an expression host. The term "operably linked" denotes herein a configuration in which a control sequence is placed at an appropriate position relative to the coding sequence of the polynucleotide sequence such that the control sequence directs the expression of the coding sequence of a peptide of the invention. A nucleic acid construct in the context of the present invention is a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a peptide coding sequence of the present invention. According to the present invention, control sequences include all components necessary for the expression of a polynucleotide encoding a peptide of the present invention. Each control sequence may be native or foreign to the nucleotide sequence encoding the polypeptide or native or foreign to each other. Such control sequences include, but are not limited to, a leader, polyadenylation sequence, pro-peptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

In yet another aspect, the invention relates to a recombinant expression vector comprising the nucleic acid construct. Illustrative recombinant expression vectors include, for example, plasmids, cosmids and viral vectors.

In another aspect, the invention relates to a recombinant host cell comprising the nucleic acid or the recombinant expression vector. The host cell may be a prokaryotic cell (such as an *Escherichia Coli* cell) or an eukaryotic cell.

In another aspect, the invention relates to a method for the production of a peptide according to the invention, comprising the steps of (i) cultivating a host cell comprising the nucleic acid construct of the invention under conditions conductive for production of the peptide; and (ii) recovering the peptide. Alternatively, the peptide of the invention may be produced by in vitro synthesis, using conventional methods as known in the art. Various commercial synthetic apparatuses are available, for example automated synthesizers by Applied Biosystems Inc., Beckman, etc. An illustrative in vitro synthesis is presented below in the experimental part, wherein the peptides are produced by standard fluorenylmethyloxy-carbonyl chloride solid-phase peptide synthesis, purified by preparative reverse phase HPLC, and analyzed by HPLC and mass spectrometry. By using synthesizers, naturally occurring amino acids may be substituted with unnatural amino acids, particularly D-isomers (or D-forms) e.g. D-alanine and D-isoleucine, diastereoisomers, side chains having different lengths or functionalities, and the like. The particular sequence and the manner of preparation will be determined by convenience, economics, purity required, and the like.

The peptides described herein are used for a broad range of applications, such as therapeutic and diagnostic applications, and are valuable laboratory tools for the performance and study of entry of viruses into cells.

Accordingly, in one aspect the invention relates to a method, in particular an in vitro method, for promoting the transduction of a cell by a virus or viral vector, comprising contacting the cell with the virus and a peptide as defined above, comprising:
  a cell-penetrating peptide (CPP) moiety; and
  a Beclin-derived peptide moiety.

In a particular embodiment, the peptide is not the peptide shown in SEQ ID NO:75 and SEQ ID NO:77.

In a particular embodiment of this aspect, the method further comprises verifying the effective transduction, or the level of transduction, of the cell by the virus. Furthermore, according to this aspect, the peptide herein disclosed is used for improving the infection or transduction of a virus or of a viral vector of interest, which has many applications as described below.

A preferred embodiment of the invention is the use of the peptide of the invention as general enhancer of viral infection or transduction efficiencies for routine laboratory practice or gene therapeutic approaches based on viral vector systems. The peptides are enhancing the entry of vectors, such as those designed for gene therapy, diagnosis, or any other purpose (such as vectors used for functional studies) into cells in vitro, ex vivo or in vivo. The peptides may be administered in combination with a viral vector, such as a vector for gene therapy or diagnosis, and mediate entry of the viral vector into the target cell. The peptides are also useful in vitro because they promote the uptake of viruses into cells. They are thus useful as a tool for studying viruses and their mechanisms of action. Another embodiment of the invention is the use of the peptide of the invention for diagnostic approaches, especially those of viruses like HIV-1 and other enveloped viruses. Therefore, the present invention also relates to an in vitro method for increasing the sensitivity of a cell-based assay for detecting the presence or absence of a virus in a sample, comprising contacting the sample, or an extract from the sample, with a cell and a peptide as defined above, wherein said peptide comprises:
  a cell-penetrating peptide (CPP) moiety; and
  a Beclin-derived peptide moiety.

Following this contacting step, the cell is cultured in appropriate culture conditions. The detection of the presence or absence of a virus may then be carried out by any method known in the art, for example by determining the level of the virus in the cell and/or in the cell culture medium.

The peptide of the invention enhances the infectious titers of virus particles and therefore enhances their cellular uptake, allowing the detection of residual viral contaminations. Therefore, it can be used to isolate viral particles from samples like serum, blood, plasma, sperm or tissues derived from subjects, in particular a human subject suspected to be infected by a virus, more specifically by an enveloped virus. The peptides according to the invention can also be used to study viral particles from water, food (avian influenza, SARS) or any (enveloped or non-enveloped) virus used in bioterrorism. Successful virus isolation could be favored several times compared with routine diagnostic methods. Preferred methods are binding affinity assays and methods to remove viruses quantitatively from solutions suspected or known to comprise viruses in order to obtain safe solutions. In such methods, the peptides of the invention are preferably covalently bound to a support or a column.

The peptides of the invention can be used to enhance in general the entry of virus particles into target cells. The peptides can also be used as a general enhancer of the infection/transduction rate of viral particles, such as non-enveloped virus particles like parvoviruses such as AAV vectors, or of virus enveloped particles such as particles that carry foreign envelope glycoproteins (pseudoparticles) like VSV-G, GALVTR, RD114TR, etc. The above peptides of the invention promote the infection rates of all analyzed enveloped virus particles. This allows performing infection experiments, especially in primary cells, that have not been feasible before. The peptides of the invention are thus useful as laboratory tools in vitro.

The peptides of the invention can also be used to enhance gene delivery rates in ex vivo or in vivo gene therapy approaches based on vector systems, in particular on non-enveloped or enveloped vector systems. Accordingly, the invention also relates to a peptide as described above for use in gene therapy for promoting the infection of an eukaryotic cell by a virus or a viral vector in a subject in need thereof. The peptide of the invention can be used in combination with a virus or viral vector in gene therapy. In particular, the invention relates to a peptide of the invention, for use in a method for the treatment of a disease by gene therapy, wherein the peptide of the invention is used in combination with a virus or viral vector comprising in its genome an appropriate therapeutic transgene for the treatment of said disease. In a particular embodiment, the treatment is carried out by administering a virus or viral vector comprising one of the transgenes described above, for use in the treatment of the corresponding disease listed above. The peptide may be for the simultaneous, separate or sequential administration with the gene therapy vector. The generation of highly infectious viral vectors for gene therapy, especially for ex vivo gene therapy of stem cells, is a difficult procedure. In particular, the transduction efficiencies of viral vectors, such as retroviral vectors (e.g. lentiviral vectors) for stem cells are low. In the presence of a peptide of the invention, however, stem cells and cell lines can be efficiently transduced with viral vectors, resulting in higher efficiencies for gene delivery into the target cell compared to samples containing no peptide. Another advantage of the peptide of the invention is that it allows the use of viral batches with low (or lower than optimal) infectious titers or that it allows the use of less viral vectors than when no peptide of the invention is implemented.

In the in vitro and ex vivo methods of the present invention, the peptide can be used either with or without prior immobilization on a solid support. Advantageously, no immobilization is required for obtaining an increased transduction efficiency.

In a particular embodiment of the in vitro methods of the invention, another transduction improving means is used together with the peptide of the invention. For example, in a particular embodiment, transduction efficiency is increased with both a peptide according to the invention and another viral transduction enhancer, such as previously described viral transduction enhancers like Vectofusin-1 (KKALL-HAALAHLLALAHHLLALLKKA-NH$_2$: SEQ ID NO:84), human fibronectin fragments (e.g. Retronectin, which is commercially available, such as from Clontech), various semen-derived enhancers of viral infection (e.g. SEVI (GIHKQKEKSRLQGGVLV-NEILNHMKRATQIPSYKKLIMY; SEQ ID NO:85), semenogelin 1 peptide SEM1(86-107) (DLNALHKTTKSQRHLGGSQQLL; SEQ ID NO:86)) or peptides derived from HIV-1 envelope glycoproteins (e.g. EF-C peptide (QCKIKQIINMWQ; SEQ ID NO:87), P16 peptide (Ac-NWFDITNWLWYIKKKK-NH2; SEQ ID NO:88)).

In another embodiment, the invention provides a kit comprising a peptide as defined above. The kit may further comprise and a virus or viral vector.

The invention is further described by means of the following examples.

EXAMPLES

Material and Methods
Peptide and Reagents

The Vectofusin-1, Tat-Scrambled, Tat-Beclin1 and its derivatives were produced by standard fluorenylmethyloxycarbonyl chloride solid-phase peptide synthesis, purified by preparative reverse phase HPLC, and analyzed by HPLC and mass spectrometry (Genecust, Dudelange, Luxembourg). 7-amino-actinomycin D (7-AAD), polybrene, protamine sulfate and Triton X-100 were obtained from Sigma-Aldrich (St-Quentin-Fallavier, France).
Cell Line Culture HCT116 cells derived from a human colorectal carcinoma (CCL-247; ATCC, Manassas, Va.) and human embryonic kidney HEK293T cells (Merten, 2011) were cultured at 37° C., 5% $CO_2$ in Dulbecco's modified Eagle's medium (DMEM+Glutamax) supplemented with 10% of heat inactivated fetal calf serum (FCS) (Life Technologies, St-Aubin, France).
Viral Vector Production and Vector Titering LVs were generated as described previously (Fenard, 2013). Briefly, HEK293T cells are transiently transfected using calcium phosphate transfection, with four plasmids: The gagpol (pKLgagpol) and rev (pKrev) expression plasmids, the transfer plasmid (pCCLsin.cPPT.hPGK.eGFP.WPRE) and the plasmid encoding either the VSV-G (pMDG) envelope glycoprotein (GP), the GALVTR GP (pBA.GALV/Ampho-Kana) or the RD114TR GP (pHCMV-RD114TR). After 24 hr of production, raw viral supernatants were harvested, filtered (0.45 µm) and frozen at −80° C. The purification of GFP-expressing VSV-G-LVs, through several membrane-based and chromatographic steps, has previously been described (Merten, 2011). Physical particle titers were determined by measuring HIV-1 p24 capsid contents using a commercial ELISA kit (Perkin Elmer, Courtaboeuf, France). Infectious titers were determined on HCT116 cells using either the detection of GFP by flow cytometry (FACSCalibur, BD Biosciences, Le Pont de Claix, France), with titers expressed as transducing units per milliliter (TU/ml), or using Q-PCR with titers expressed as infectious genome per ml (ig/ml)(Merten, 2011).
Cell Line Transduction For lentiviral transduction, HCT116 cells were transduced in 48-well plates with the desired amount of lentiviral vector supernatant in absence or presence of culture additives during six hours. Next, cells were incubated in fresh medium and further cultured for 3 to 4 days.

For transduction experiments performed with recombinant adeno-associated virus serotype 8 (AAV8-GFP), 293T cells were transduced in 12-well plates with a multiplicity of infection (MOI) of 1000 in absence or presence of culture additives. After 16 hr, cells were washed and further cultured in fresh medium for 24 hr. In these experiments, transduction efficiencies were evaluated by following GFP expression using flow cytometry (FACSCalibur, BD Biosciences).
Human CD34+ Cells Culture and Transduction Umbilical cord blood (UCB) samples were collected with informed consent after uncomplicated births at the Centre Hospitalier Sud Francilien, Evry, France, in accordance with international ethical principles and French national law (bioethics law no 2011-814) under declaration No DC-201-1655 to the French Ministry of Research and Higher Studies. Human CD34+ cells were isolated by immunomagnetic selection (Miltenyi Biotec, Paris, France). The preactivation of hCD34+ cells was performed overnight as previously described (Ingrao et al., 2014). Pre-activated cells were plated in 96-well plates and the transduction was initiated by adding the desired amount of LV particles mixed with or without the peptides of interest. At 6 hr post-transduction, reactions were diluted by adding differentiation medium in each well. After 4-6 days, cellular mortality and transduction efficiency were evaluated respectively by 7-AAD labeling and measurement of GFP expression.
Viral Pull Down Assay The pull-down of LV particles in presence of culture additives was adapted from a previously described protocol (Yolamanova, 2013). Briefly, The VSV-G-LV supernatant was diluted to 100 ng/ml of p24 with X-Vivo20 medium equilibrated at room temperature. Next, 1.5 ml tubes were loaded with 500 µl of LV suspension in absence or presence of 10 µM of the indicated culture additive. After homogenization, samples were centrifuged at low speed (15,000 g) for 5 min at room temperature. Then, the supernatant was discarded, the pellet suspended in 100 µl of fresh medium and frozen at −20° C. For each condition, the amount of pelleted p24 was evaluated using a commercial HIV-1 p24 ELISA kit as described above.
Adhesion and BLAM-LV Fusion Assay The protocol for LV adhesion to target cells was adapted from a previous study (Fenard, 2013). Briefly, HCT116 cells were pre-incubated 30 min at 37° C. in absence or presence of Tat-Scrambled or Tat-Beclin1 (5 µM). Then, cells were further incubated 2.5 hr at 4° C. with viral supernatants in absence or presence of culture additives. Next, cells were washed 3 times with cold PBS1× and lysed in PBS1× containing 1% Triton X-100 and a protease cocktail inhibitor, Complete (Roche diagnostics, Meylan, France). p24 contents in lysates were evaluated using a commercial HIV-1 p24 ELISA kit and data were normalized to total protein content using the DC protein assay (Biorad, Ivrysur-Seine, France). For the viral fusion assay (BLAM-LV) assay, the protocol was extensively described previously (Ingrao et al., 2014).

CFC Assay

CFC assays were performed in duplicate by plating 500 transduced or untransduced cells per milliliter of Methocult (H4434, Stemcell Technologies), according to the manufacturer's instructions. After 2 weeks of culture, burst-forming unit, erythroid (BFU-E); colony-forming unit, granulocyte-monocyte (CFU-GM) and colony-forming unit, granulocyte, erythrocyte, macrophage, megakaryocyte (CFU-GEMM) were counted using an inverted microscope with standard visual criteria.

Autophagy Assay Based on Imaging Flow Cytometry (ImageStream)

HEK293T cells were transfected with the pBABE-puro-mCherry-eGFP-LC3 expression plasmid using the transient calcium phosphate transfection method. Cells (5×10E5 cells/well), were incubated in the absence or presence of Tat-Beclin1 (5 µM) or in an Earle's Balanced Salt solution (EBSS) for 6 h at 37° C., 5% $CO_2$. Next, cells were washed in PBS 1×, fixed (1.2% PFA) and analyzed using the ImageStream (Amnis corporation, Seattle, Wash., USA). Images of cells were acquired in bright field channel, in mCherry-fluorescence channel, and finally in the SSC channel (742 nm) using the 40× magnitude objective and lowest flow velocity to optimize sensitivity. Once, acquired, images were treated with Ideas® software. Focused images were gated on a histogram displaying Gradient_RMS feature values in the bright field channel between 40 and 90. Then a scatter plot of Area versus Aspect Ratio (in the bright field channel) was used to gate on single cells and remove doublets of cells. Once gated on single cells, the number of spot on each cell was counted in mCherry channel, using the automatic spot counting wizard included in Ideas® software. Data were exported as text files and processed with GraphPad Prism.

Results and Discussion

Low Doses of Tat-Beclin1 Strongly Improved Lentiviral Transduction of Cell Lines with Various Pseudotypes.

To evaluate the effect of the TB1 (SEQ ID NO:75) peptide on lentiviral transduction, HCT116 cells were transduced with lentiviral vectors (LVs) pseudotyped with the broadly used VSV-G glycoprotein envelope (VSV-G-LVs) in presence of low or high doses of TB1 or the control peptide Tat-Scrambled (TS) (FIG. 1A). Interestingly, the use of low doses of TB1 strongly improved lentiviral transduction (10-fold). Furthermore, the TB1 effect is not saturable over a one log concentration of VSV-G-LV, from 10E5 to 10E6 TU/ml (corresponding to an MOI of 0.5 to 5), reaching up to 84% of transduction efficiency (FIG. 1B).

A great advantage of using LVs for gene transfer is their capacity to support pseudotyping with numerous heterologous envelope glycoproteins for specific cell targeting (Levy, 2015). Therefore, the effect of TB1 was evaluated on various LV pseudotypes, namely modified gibbon ape leukemia virus glycoprotein-pseudotyped LV (GALVTR-LV) and modified RD114 feline endogenous retrovirus glycoprotein-pseudotyped LV (RD114TR-LV). Very importantly, these hematopoietic-tropic pseudotypes are well known for their requirement of culture additives to promote an efficient transduction. On adherent cell lines, the classical soluble additives used to promote LVs are the polybrene, the protamine sulfate or the recently identified Vectofusin-1 (Fenard, 2013). As shown in FIG. 1C, TB1 is promoting GALVTR and RD114TR-LV transduction to an extent comparable to other culture additives. TB1 is therefore an efficient lentiviral transduction enhancer other a large panel of cell lines and lentiviral pseudotypes.

Tat-Beclin1 Promotes a Safe Lentiviral Transduction of Hematopoietic Stem/Progenitor Cells.

Although it is interesting to promote lentiviral transduction of cell lines for fundamental research, another strong interest is to optimize current clinical protocols of lentiviral transduction, targeting hematopoietic stem/progenitor cells (HSPCs) for ex vivo gene therapy approaches. As shown in FIG. 2A, highly purified VSV-G-LV particles were used to transduce human CD34+ HSPCs. In presence of TB1, a two-fold increase in lentiviral transduction was observed. The optimal dose of TB1 to promote lentiviral transduction of HSPCs was defined around 10 µM (FIG. 2A-B).

Since it has been previously shown that the TB1 peptide is able to trigger a specific cell death called autosis (Liu, 2013), safety studies have been performed on HSPCs. For that, a colony forming cell (CFC) assay was implemented from human CD34+ cells exposed to optimal concentrations of Retronectin, TS or TB1 peptide during lentiviral transduction. For these experiments, we used highly purified VSV-G-LV to transduce CD34+ cells because these vectors exhibit no measurable hematopoietic toxicity in this assay (Merten, 2011). As shown in FIG. 2C, there was no evidence of toxicity from any of the culture additives used in the assay. Exposure of CD34+ cells to TB1 did not affect their subsequent growth as CFC and myelo-erythroid differentiation.

Tat-Beclin1 is Acting on the Adhesion and Fusion Steps of LVs with Target Cell Membranes.

The LV entry into target cells is a rate limiting step. Therefore, we decided to test whether low doses of TB1 are capable to enhance adhesion and fusion of LVs with target cell membranes. For that, the BLAM-LV assay was used (Ingrao, 2014). As shown in FIG. 3A, TB1 strongly increased the viral fusion step, either with cell lines (HCT116) or relevant primary cells like hCD34+ HSPCs. Next, by quantifying the number of viral particles interacting with target cells at 4° C., we have shown that the level of viral adhesion strongly increased in presence of TB1, to a level comparable to the control condition using Vectofusin-1 (FIG. 3B). However, using a viral pull-down assay, we have shown that this increase in viral adhesion is not the consequence of a TB1-induced aggregation of viral particles, like it is the case for Vectofusin-1, a nanofibrillar peptide (FIG. 3C). Therefore, the TB1 peptide is capable to increase the viral adhesion and fusion step through a molecular mechanism that is not involving the aggregation of viral particles.

Design and Evaluation of Numerous Tat-Beclin1 Variants on Lentiviral Transduction.

To evaluate the specificity of action of TB1 on lentiviral transduction, the Tat transduction domain (Tat) and the 267-284 modified beclin1 domain (Bec) have been synthesized and tested during the transduction of HCT116 cells with VSV-G-LVs. As shown in FIG. 4, neither Tat nor Bec peptides are capable to promote lentiviral transduction. Therefore, the positive effect of TB1 on lentiviral transduction is not due to the cell-penetrating peptide (CPP) activity of Tat. Also, the Beclin1 domain has to be linked to a transduction domain to perform its effect, suggesting that it is acting inside the cell, certainly through the specific interaction with the GAPR-1 protein, as described in Shoji-Kawata study or through the interaction with another cellular partner that remains to be identified.

To increase its peptide solubility, Shoji-Kawata and colleagues incorporated three mutations in the 267-284 Beclin1 domain of TB1, namely H275E, S279D and Q281E (WO2013/119377, Shoji-Kawata et al. 2013). To evaluate the influence of these mutations on the viral transduction enhancer activity, the wild-type 267-284 domain of the human Beclin1 protein has been fused to Tat (Tat-BecWT). As shown in FIG. 4, Tat-BecWT is capable to promote lentiviral transduction as efficiently as TB1 at a concentration of 2.5 µM. However, this peptide is no longer active at a concentration of 5 µM compared to TB1. It is not excluded that these three mutations may improve the interaction with the GAPR-1 protein or another key partner, leading to a better viral transduction enhancer activity. Indeed, these mutations increase the interaction of this Beclin1 domain to a viral factor, the HIV-1 Nef protein, by 25 to 30% (see Shoji-Kawata et al. 2013, supplementary FIG. 1d).

To further understand the action mechanism of TB1 on viral transduction, the role of the two phenylalanine residues in the TB1 peptide has been evaluated. Previously, Shoji-Kawata and colleagues have shown that Tat-Bec(F270S) and Tat-Bec(F274S) peptides are no longer able to induce the autophagy pathway (Shoji-Kawata et al. 2013). In our viral transduction experiments, these peptides are also unable to promote lentiviral transduction (FIG. 4), suggesting that phenylalanine residues are critical for any of these functions.

Numerous cell-penetrating peptides (CPPs) have been discovered over the last years (Milletti et al. 2012). Therefore, it could be interesting to test a CPP different from the broadly used Tat peptide. One interesting candidate is MAP (Model Amphipathic Peptide). We designed a MAP-Scrambled negative control and a MAP-Beclin1 peptide (with the MAP moiety having the sequence shown in SEQ ID NO:4). As shown in FIG. 4, MAP-Beclin1 (SEQ ID NO:76) is as efficient as TB1 to promote lentiviral transduction, suggesting that various CPPs could be used to allow the modified Beclin1 domain entry into the target cell cytoplasm.

The modified Beclin1 domain of the TB1 peptide is corresponding to amino acid residues 267 to 284 of the human Beclin1 protein (*Homo sapiens*, NP_003757). This domain is described has a human GAPR-1 and HIV-1 Nef protein binding domain. However, the optimal Beclin1 peptide sequence capable to promote the lentiviral transduction with high efficiency has not been evaluated. For that, numerous peptides have been designed (FIG. 5A). These peptides are allowing a better coverage of the Beclin1 protein. For instance, Tat-Bec(250-282) (SEQ ID NO:81) is fully covering the α1 helix, the L1 loop and the 01 sheet (based on the crystal structure, Huang et al. 2012). While Tat-Bec(274-298) (SEQ ID NO:82) is fully covering the β1 and β2 sheet and the L2 loop (FIG. 5A). All these TB1 derivatives have been tested in a lentiviral transduction assay. As shown in FIG. 5B, all the peptides are capable to promote lentiviral transduction although with a different extent. At 2.5 µM, most of the derivatives are a lot more efficient than TB1, except for Tat-Bec(274-298). However, at 5 µM, it looks like the more the peptide sequence is shifting to the C-terminal side of the protein, the less it is effective on lentiviral transduction. Dose response experiments using Tat-Bec (267-296) (SEQ ID NO:83) are showing that very low doses of this peptide (down to 1 µM) are capable to promote optimal lentiviral transduction (FIG. 5C). Interestingly, the peptide containing the wild type sequence of the 267-296 Beclin1 fragment (Tat-Bec(267-296)WT) (SEQ ID NO:80) is promoting the lentiviral transduction but less efficiently than the Tat-Bec(267-296) peptide containing the three modifications H275E, S279D and Q281E (FIG. 5D). This result is reminiscent to the one obtained with Tat-BecWT (SEQ ID NO:77) (FIG. 4). Finally, Tat-Bec(267-296)dGG (SEQ ID NO:74), a peptide variant of Tat-Bec(267-296) in which the GG linker has been deleted, is increasing by nearly five folds the level of viral transduction, suggesting that this linker is not strictly dependent to observe a positive effect of the peptide on lentiviral transduction.

Altogether, these beclin1 domain variants highlight a very important role of the region covering amino acid residues 270 to 282 in the human Beclin1 sequence to promote lentiviral transduction. The most performant peptide at a low dose (2.504) is Tat-Bec(250-282), suggesting an important role of the α1 helix, the L1 loop and the 131 sheet domains.

Evaluation of TB1 Action on Adeno-Associated Viral Vectors

Adeno-associated vectors (AAVs) are among the most frequently used viral vectors for gene therapy approaches. Among the different serotypes, AAV-8 has been successfully used in the clinic and hold great promise for liver-directed gene therapy (Nathwani et al, 2014). Hence, the effect of TB1 on AAV8 transduction efficiency has been evaluated in vitro. As shown in FIG. 6, TB1 is capable to enhance recombinant AAV8 infectivity in a dose dependent manner, while the Tat-Scrambled control peptide has no effect. This result highlights the broad spectrum of action of TB1, acting both on enveloped and non-enveloped viral vectors.

Evaluation of TB1 Optimal Dose on the Autophagy Process

To better understand the mechanism of action of TB1, we sought to investigate whether the increase in lentiviral transduction is the consequence of the activation of the autophagy process. To monitor autophagy at the single cell level, HEK293T cells have been transfected with a plasmid expressing the mCherry-eGFP-LC3 fusion protein. Next, cells were incubated with TB1 (5 µM) or the EBSS starvation solution and analyzed with an imaging flow cytometer. As expected, EBSS is increasing the number of autophagolysosomes (mCherry spots) per cell (FIG. 7). At the opposite, the number of autophagolysosomes in TB1-treated HEK293T cells is comparable to the control condition in absence of peptide (None). These data suggest that the improvement of lentiviral transduction observed in presence of TB1 is certainly not the consequence of an induction of the autophagy flux.

Design and Evaluation of Tat-Beclin2 on Lentiviral Transduction.

A sequence alignment of the human Beclin 1 and Beclin 2 proteins is showing homologies in the ECD domain. Therefore, we decided to design a Tat-Bec2WT peptide, the fusion of the Tat (47-57) transduction peptide with the human Beclin2 ECD$_{249-266}$ domain (FIG. 8A). Since TB1 is containing three mutations (H275E, S279D and Q281E), the Tat-BecWT peptide corresponding to the fusion of the Tat (47-57) peptide with the wild type human Beclin1 ECD$_{267-284}$ domain was also designed and is represented in the sequence alignment (FIG. 8A). These three peptides have been tested for their capacity to promote lentiviral production over a large range of concentrations. As shown in FIG. 8B, all the peptides are capable to efficiently promote lentiviral transduction, but with a lot of variability in their optimal dose: 3 µM for TB1, 1 µM for Tat-BecWT and 500 nM for Tat-Bec2WT. Only 100 nM of Tat-Bec2WT are capable to increase lentiviral transduction by three-folds, from 10 to 30% (8B), while TB1 and Tat-BecWT have no effect at this concentration. Tat-Scr2WT, a scrambled version of Tat-Bec2WT, is promoting lentiviral transduction, but at doses corresponding to a decrease in the magnitude of the effect for Tat-Bec2WT, certainly a Tat-dependent activity. In conclusion, Tat-Bec2WT is a potent enhancer of lentiviral transduction at very low doses.

REFERENCES

D'Costa, J., S. G. Mansfield, and L. M. Humeau. 2009. Lentiviral vectors in clinical trials: Current status. *Curr. Opin. Mol. Ther.* 11:554-564.

Davis, H. E., M. Rosinski, J. R. Morgan, and M. L. Yarmush. 2004. Charged polymers modulate retrovirus transduction via membrane charge neutralization and virus aggregation. *Biophys. J.* 86:1234-1242.

Fenard, D., D. Ingrao, A. Seye, J. Buisset, S. Genries, S. Martin, A. Kichler, and A. Galy. 2013. Vectofusin-1, a new viral entry enhancer, strongly promotes lentiviral transduction of human hematopoietic stem cells. *Mol. Ther. Nucleic Acids* 2:e90.

He, C., Y. Wei, K. Sun, B. Li, X. Dong, Z. Zou, Y. Liu, L N. Kinch, S. Khan, S. Sinha, R J. Xavier, N V. Grishin, G. Xiao, E L. Eskelinen, P E. Scherer, J L. Whistler and B. Levine. 2013. Beclin 2 Functions in Autophagy, Degradation of G Protein-Coupled Receptors, and Metabolism. *Cell.* 154(5):1085-99.

Huang, W., W. Choi, W. Hu, N. Mi, Q. Guo, M. Ma, M. Liu, Y. Tian, P. Lu, F. L. Wang, H. Deng, L. Liu, N. Gao, L. Yu, and Y. Shi. 2012. Crystal structure and biochemical analyses reveal Beclin 1 as a novel membrane binding protein. *Cell Res.* 22:473-489.

Ingrao, D., S. Majdoul, A. K. Seye, A. Galy, and D. Fenard. 2014. Concurrent Measures of Fusion and Transduction Efficiency of Primary CD34+ Cells with Human Immunodeficiency Virus 1-Based Lentiviral Vectors Reveal Different Effects of Transduction Enhancers. *Hum. Gene Ther. Methods* 25:48-56.

Levy, C., E. Verhoeyen, and F. L. Cosset. 2015. Surface engineering of lentiviral vectors for gene transfer into gene therapy target cells. *Curr. Opin. Pharmacol.* 24:79-85.

Liu, Y., S. Shoji-Kawata, R. M. Sumpter, Jr., Y. Wei, V. Ginet, L. Zhang, B. Posner, K. A. Tran, D. R. Green, R. J. Xavier, S. Y. Shaw, P. G. Clarke, J. Puyal, and B. Levine. 2013. Autosis is a Na+,K+-ATPase-regulated form of cell death triggered by autophagy-inducing peptides, starvation, and hypoxia-ischemia. *Proc. Natl. Acad. Sci. U.S.A.* 110:20364-20371.

Merten, O. W., S. Charrier, N. Laroudie, S. Fauchille, C. Dugue, C. Jenny, M. Audit, M. A. Zanta-Boussif, H. Chautard, M. Radrizzani, G. Vallanti, L. Naldini, P. Noguiez-Hellin, and A. Galy. 2011. Large-scale manufacture and characterization of a lentiviral vector produced for clinical ex vivo gene therapy application. *Hum. Gene Ther.* 22:343-356.

Milletti, F. 2012. Cell-penetrating peptides: classes, origin, and current landscape. *Drug Discov. Today* 17:850-860.

Munch, J., E. Rucker, L. Standker, K. Adermann, C. Goffinet, M. Schindler, S. Wildum, R. Chinnadurai, D. Rajan, A. Specht, G. Gimenez-Gallego, P. C. Sanchez, D. M. Fowler, A. Koulov, J. W. Kelly, W. Mothes, J. C. Grivel, L. Margolis, O. T. Keppler, W. G. Forssmann, and F. Kirchhoff. 2007. Semen-derived amyloid fibrils drastically enhance HIV infection. *Cell* 131:1059-1071.

Nathwani, A. C., U. M. Reiss, E. G. Tuddenham, C. Rosales, P. Chowdary, J. McIntosh, M. Della Peruta, E. Lheriteau, N. Patel, D. Raj, A. Riddell, J. Pie, S. Rangarajan, D. Bevan, M. Recht, Y. M. Shen, K. G. Halka, E. Basner-Tschakarjan, F. Mingozzi, K. A. High, J. Allay, M. A. Kay, C. Y. Ng, J. Zhou, M. Cancio, C. L. Morton, J. T. Gray, D. Srivastava, A. W. Nienhuis, A. M. Davidoff. Long-term safety and efficacy of factor IX gene therapy in hemophilia B. 2014. *N. Engl. J. Med.* 371(21):1994-2004.

Novelli, E. M., L. Cheng, Y. Yang, W. Leung, M. Ramirez, V. Tanavde, C. Enger, and C. I. Civin. 1999. Ex vivo culture of cord blood CD34+ cells expands progenitor cell numbers, preserves engraftment capacity in nonobese diabetic/severe combined immunodeficient mice, and enhances retroviral transduction efficiency. *Hum. Gene Ther.* 10:2927-2940.

Pollok, K. E., and D. A. Williams. 1999. Facilitation of retrovirus-mediated gene transfer into hematopoietic stem and progenitor cells and peripheral blood T-lymphocytes utilizing recombinant fibronectin fragments. *Curr. Opin. Mol. Ther.* 1:595-604.

Roan, N. R., J. Munch, N. Arhel, W. Mothes, J. Neidleman, A. Kobayashi, K. Smith-McCune, F. Kirchhoff, and W. C. Greene. 2009. The cationic properties of SEVI underlie its ability to enhance human immunodeficiency virus infection. *J. Virol.* 83:73-80.

Rodrigues, T., M. J. Carrondo, P. M. Alves, and P. E. Cruz. 2007. Purification of retroviral vectors for clinical application: biological implications and technological challenges. *J. Biotechnol.* 127:520-541.

Sandrin, V., B. Boson, P. Salmon, W. Gay, D. Negre, R. Le Grand, D. Trono, and F. L. Cosset. 2002. Lentiviral vectors pseudotyped with a modified RD114 envelope glycoprotein show increased stability in sera and augmented transduction of primary lymphocytes and CD34+ cells derived from human and nonhuman primates. *Blood* 100:823-832.

Shoji-Kawata, S., R. Sumpter, M. Leveno, G. R. Campbell, Z. Zou, L. Kinch, A. D. Wilkins, Q. Sun, K. Pallauf, D. MacDuff, C. Huerta, H. W. Virgin, J. B. Helms, R. Eerland, S. A. Tooze, R. Xavier, D. J. Lenschow, A. Yamamoto, D. King, O. Lichtarge, N. V. Grishin, S. A. Spector, D. V. Kaloyanova, and B. Levine. 2013. Identification of a candidate therapeutic autophagy-inducing peptide. *Nature* 494:201-206.

Yolamanova, M., C. Meier, A. K. Shaytan, V. Vas, C. W. Bertoncini, F. Arnold, O. Zirafi, S. M. Usmani, J. A. Muller, D. Sauter, C. Goffinet, D. Palesch, P. Walther, N. R. Roan, H. Geiger, O. Lunov, T. Simmet, J. Bohne, H. Schrezenmeier, K. Schwarz, L. Standker, W. G. Forssmann, X. Salvatella, P. G. Khalatur, A. R. Khokhlov, T. P. Knowles, T. Weil, F. Kirchhoff, and J. Munch. 2013. Peptide nanofibrils boost retroviral gene transfer and provide a rapid means for concentrating viruses. *Nat. Nanotechnol.* 8:130-136.

The invention claimed is:

1. An in vitro method for promoting transduction of a mammalian cell by a virus or viral vector, comprising contacting the mammalian cell with
   the virus or the viral vector and
   a CPP-Beclin peptide, comprising:
      a cell-penetrating peptide (CPP) moiety, wherein the CPP moiety is a HIV-1 TAT or MAP; and
      a peptide moiety based on Beclin 1 or Beclin 2 which comprises SEQ ID NO:65 or SEQ ID NO:89, wherein the SEQ ID NO:89 comprises a sequence of general formula (I):

N1 N2 N3 N4 N5 N6 T F N9 I N11 N12 N13 G N15 N16 N17 N18 (I)

wherein:

N1 is a polar amino acid or is I;

N2 is a polar amino acid;

N3 is a hydrophobic amino acid or C;

N4 is a hydrophobic amino acid;

N5 is a polar amino acid;

N6 is a hydrophobic amino acid;

N9 is a polar amino acid;

N11 is W, S, G or R;

N12 is a polar amino acid or is V;

N13 is a polar amino acid or is A;

N15 is Q, P, S or E;

N16 is a hydrophobic amino acid;

N17 is a hydrophobic amino acid;

N18 is T, V or I;

and the SEQ ID NO:65 comprises a sequence of general formula (II):

N1 N2 N3 F N5 N6 T F N9 I N11 N12 N13 G N15 N16 N17 N18 (II)

wherein:

N1 is a polar amino acid or is I;

N2 is a polar amino acid;

N3 is a hydrophobic amino acid;

N5 is a polar amino acid;

N6 is a hydrophobic amino acid;

N9 is a polar amino acid;

N11 is W, S, G or R;

N12 is a polar amino acid or is V;

N13 is a polar amino acid or is A;

N15 is P or S;

N16 is a hydrophobic amino acid;

N17 is a hydrophobic amino acid;

N18 is a hydrophobic amino acid;

wherein the CPP-Beclin peptide is present at a concentration sufficient to promote transduction of the mammalian cell with the virus or viral vector but which does not induce autosis, wherein the virus or viral vector and the CPP-Beclin peptide are simultaneously in contact with the cell, and wherein the virus or viral vector is a lentivirus, an adeno-associated virus (AAV), a lentiviral vector or an AAV vector.

2. The in vitro method of claim 1, wherein the lentivirus is a pseudotyped lentivirus.

3. The in vitro method of claim 1, wherein the mammalian cell is a hematopoietic stem/progenitor cell.

4. The in vitro method according to claim 1, further comprising contacting the cell with at least one viral transduction enhancer.

5. The in vitro method according to claim 1, wherein the concentration ranges from 0.01 to 20 μM.

6. The in vitro method of claim 3, wherein the hematopoietic stem/progenitor cell is a hCD34+ cell.

7. The in vitro method of claim 4, wherein the at least one viral transduction enhancer is vectofusin, a human fibronectin fragment, a semen-based enhancer of viral infection or a peptide from an HIV-1 envelope glycoprotein.

8. The in vitro method of claim 1, wherein in general formula (I):

N1 is T or I,

N2 is N, D or S,

N3 is V, C or I,

N4 is F or L,

N5 is N, T, S, R or Q,

N6 is A or V,

N9 is H, E or T,

N11 is W;

N12 is H, V, D, Q or E,

N13 is S, E, D, A,

N15 is P;

N16 is F, L, V or I,

N17 is G, A or P, and

N18 is V;

and in general formula (II):

N1 is T or I,

N2 is N, D or S,

N3 is V, C or I,

N5 is N, T, S, R or Q,

N6 is A or V,

N9 is E or T,

N11 is W,

N12 is H, V, D, Q or E,

N 13 is S, E, D, A,

N15 is P,

N16 is L, V or I,

N17 is G, A or P and

N18 is V or I.

9. The in vitro method of claim 8, wherein the peptide moiety based on Beclin 1 or Beclin 2 has an amino acid sequence as set forth in one of SEQ ID NOS:65-73 or in SEQ ID NO:89.

10. The in vitro method of claim 1 wherein the CPP-Beclin peptide is a fusion peptide and comprises a dipeptide linker between the CPP moiety and the peptide moiety based on Beclin 1 and Beclin 2.

11. The in vitro method of claim 10 wherein the CPP-Beclin peptide has an amino acid sequence selected from the group consisting of:

YGRKKRRQRRRGGTNVFNATFEIWHDGEFGT, (SEQ ID NO: 75)

KLALKLALKALKAALKAGTNVFNATFEIWHDGEFGT, (SEQ ID NO: 76)

YGRKKRRQRRRGGTNVFNATFHIWHSGQFGT, (SEQ ID NO: 77)

YGRKKRRQRRRGGYAQTQLDKLKKTNVFNATFEIWHDGEFGT, (SEQ ID NO: 78)

YGRKKRRQRRRGGTNVFNATFEIWHDGEFGTINNFRLGRLPSV, (SEQ ID NO: 79)

YGRKKRRQRRRGGTNVFNATFHIWHSGQFGTINNFRLGRLPSV, (SEQ ID NO: 80)

YGRKKRRQRRRGGVENQMRYAQTQLDKLKKTNVFNATFEIWHDGEF, (SEQ ID NO: 81)

YGRKKRRQRRRGGFEIWHDGEFGTINNFRLGRLPSVPV, (SEQ ID NO: 82)

YGRKKRRQRRRGGFNATFEIWHDGEFGTINNFRLGRLPSVPV (SEQ ID NO: 83)
and

YGRKKRRQRRRGGINCFTATFEIWVEGPLGV. (SEQ ID NO: 91)

\* \* \* \* \*